US006293162B1

(12) United States Patent
Mathur et al.

(10) Patent No.: US 6,293,162 B1
(45) Date of Patent: Sep. 25, 2001

(54) FLUID SELECTION VALVE FOR A MODULAR AUTOMATED DIAGNOSTIC APPARATUS

(75) Inventors: Vijay Mathur, Burlington; Tyler Cote, Acton, both of MA (US); Ronald Jones, Newton, NH (US); Jane Sun, Acton, MA (US); Steve Rettew, Harvard, MA (US); Chen Yi, Woburn, MA (US); Tony Mao, Natick, MA (US); Will Whelan, Arlington, MA (US); Ken Galano, Wrenham, MA (US); Richard Dussault, North Attleboro, MA (US)

(73) Assignee: Medica Corporation, Bedford, MA (US)

( * ) Notice: Subject to any disclaimer, the term of this patent is extended or adjusted under 35 U.S.C. 154(b) by 0 days.

(21) Appl. No.: 09/350,247

(22) Filed: Jul. 8, 1999

Related U.S. Application Data

(62) Division of application No. 09/118,683, filed on Jun. 30, 1998, now Pat. No. 5,983,734.
(60) Provisional application No. 60/053,265, filed on Jul. 21, 1997.

(51) Int. Cl.[7] ....................................................... G01N 1/00
(52) U.S. Cl. ............................................................. 73/864.22
(58) Field of Search ................................. 73/64.56, 1.02, 73/1.03, 864.21–864.25, 864.81, 865.6, 865.8, 431, 866.5, 863.71, 863.72, 864.22; 422/100, 82.01–82.04; 324/438; 204/422, 423, 407

(56) References Cited

U.S. PATENT DOCUMENTS

| 4,499,053 | * | 2/1985 | Jones ................................. 73/864.25 |
| 5,194,226 | * | 3/1993 | Tomoff et al. .................... 73/864.25 |
| 5,408,891 | * | 4/1995 | Barber et al. ..................... 73/864.22 |

* cited by examiner

Primary Examiner—Robert Raevis
(74) Attorney, Agent, or Firm—Gary D. Clapp, Esq.

(57) ABSTRACT

A modular automated diagnostic analyzer having a fluid entry module for sample aspiration, a valve module for selecting fluids and a pump module for fluidic movement, so that a biological sample does not come into contact with the valve system through which calibrants and air are introduced to the fluid path. The fluid entry module encloses an aspiration tube rotatably and slidably engaged with the analysis mechanism chassis to move to different positions for the introduction of calibration and cleaning fluids and the aspiration of fluids into the analysis apparatus from different tpes of sample containers. A wiping seal removes residues of aspirated fluids from the exterior surfaces of the aspiration tube with the residue being aspirated into the analysis apparatus for disposal. Sensor modules mounted in a sensor chamber are structured to mechanically stack and interlock and each sensor module includes a fluid tight sealed passage and a sensor element. A fluid selection valve of highly polished ceramic material allows a valve cylinder passage to be selectively connected to fluid sources. A self-contained reagent pouch housing contains calibrants including tonometered calibrants in reagent pouches wherein each pouch wall includes multiple layers of materials wherein at least one layer is a thin, flexible glass material. The walls are extended to form a filler neck sealed by heat and pressure along a sealing line below a filler line so that no bubbles are trapped in the reagent pouch.

5 Claims, 11 Drawing Sheets

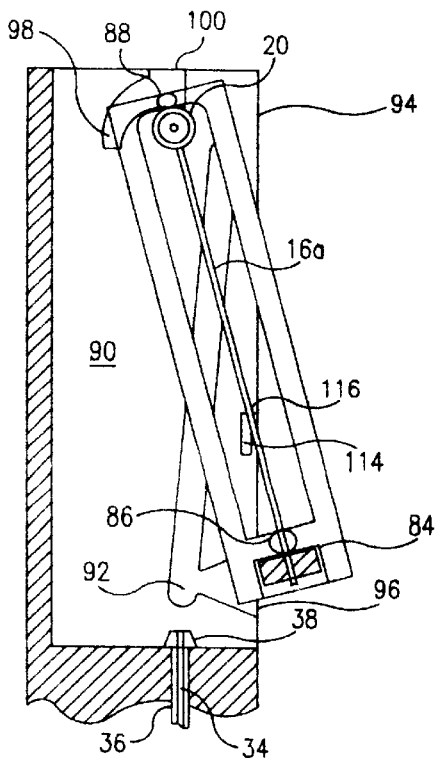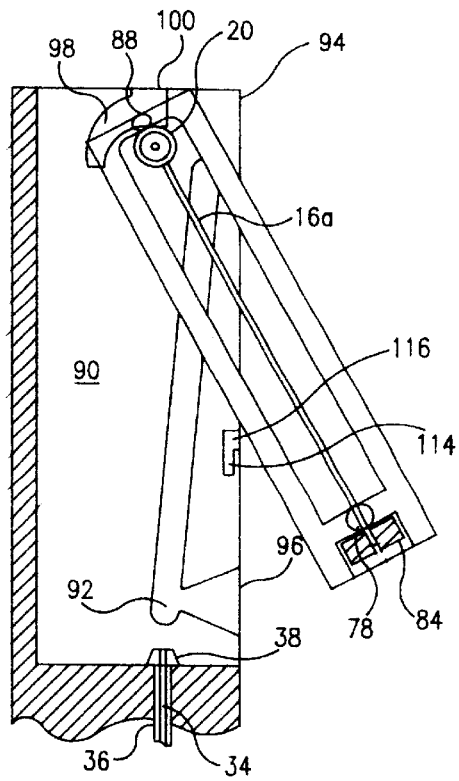
FIG. 5A   FIG. 5B
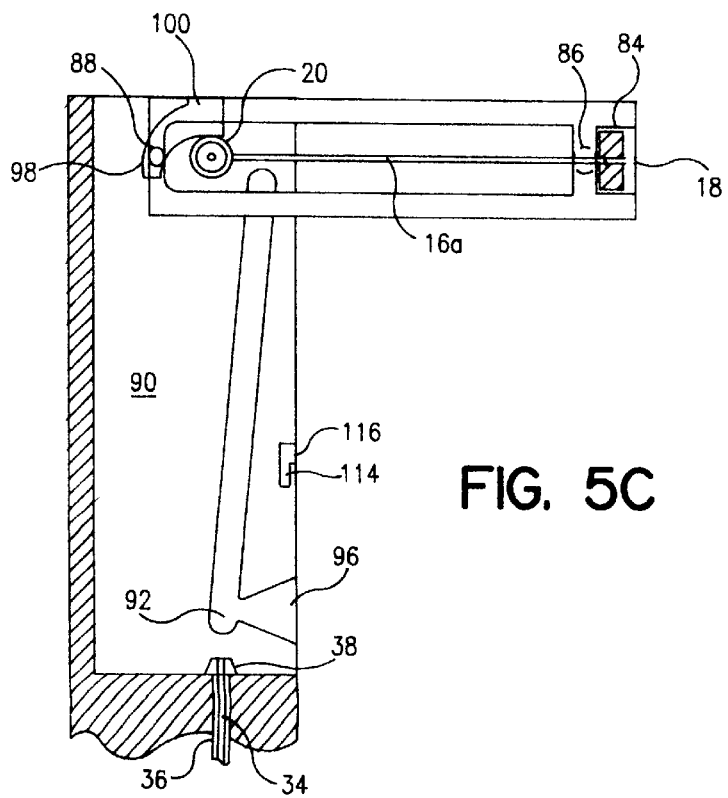
FIG. 5C

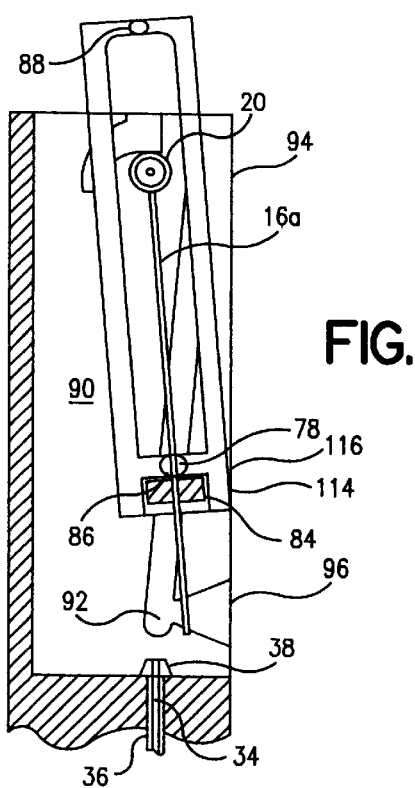
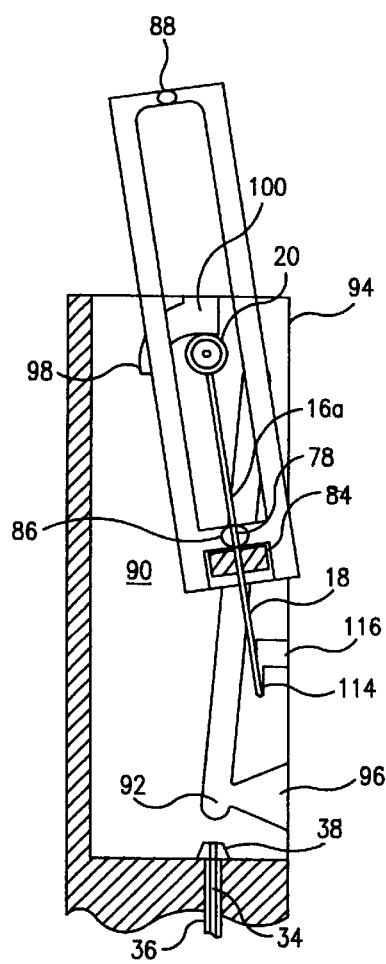
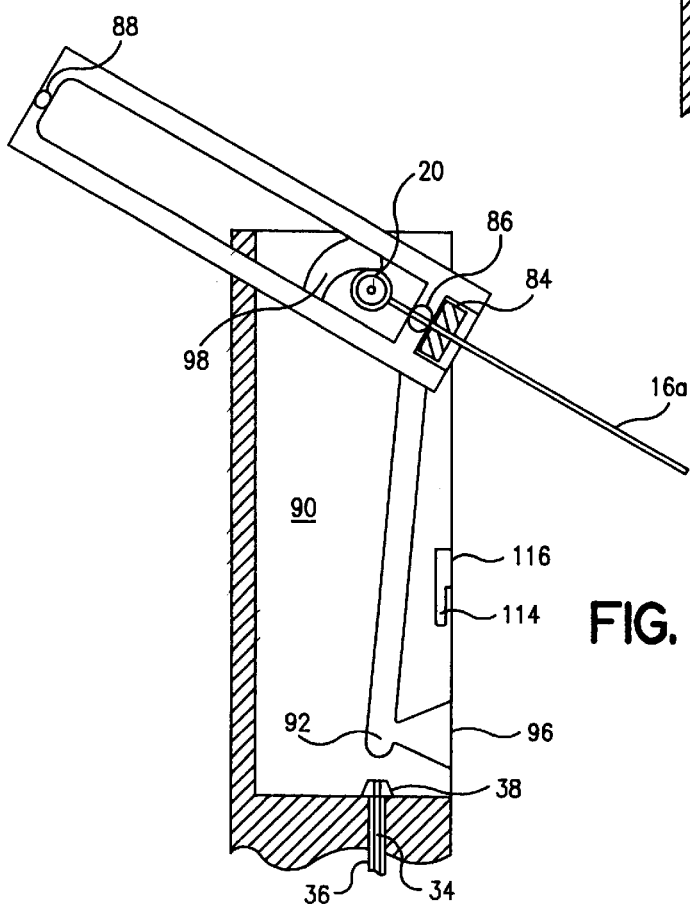

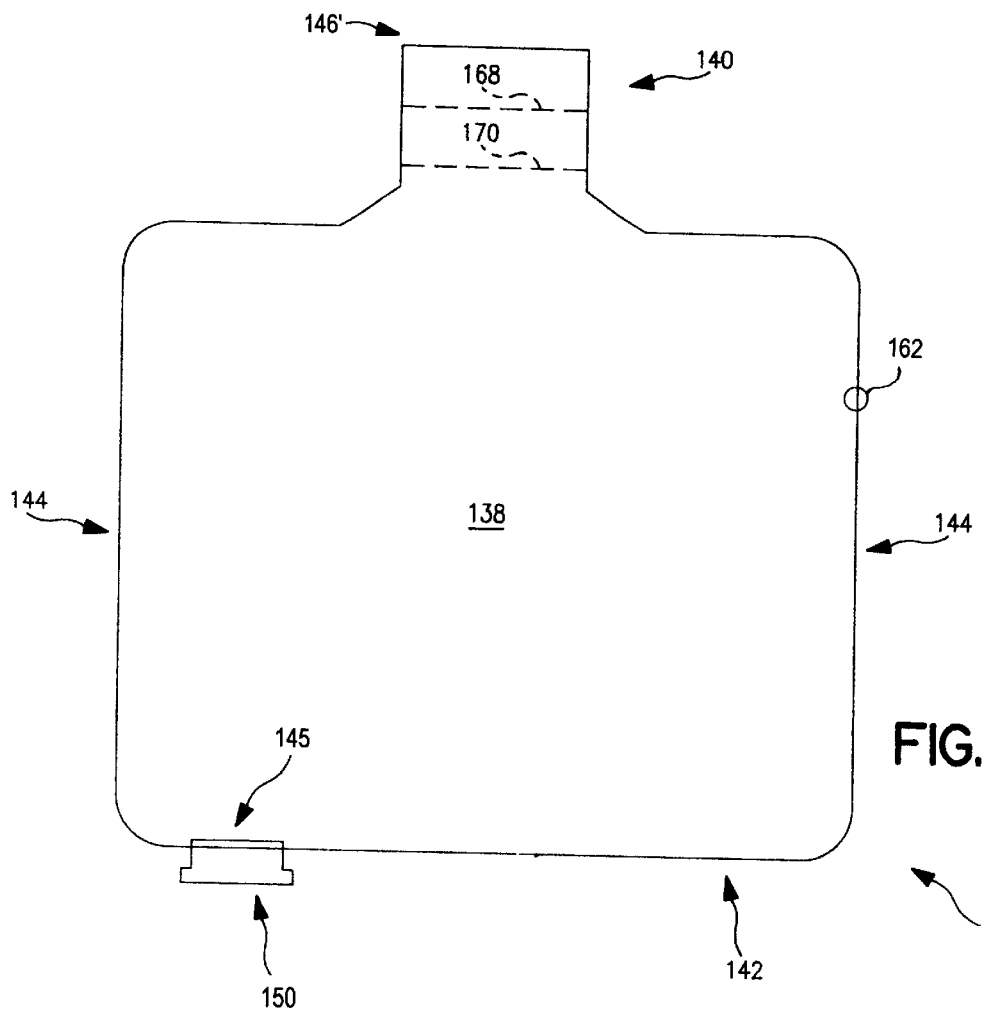
FIG. 9A
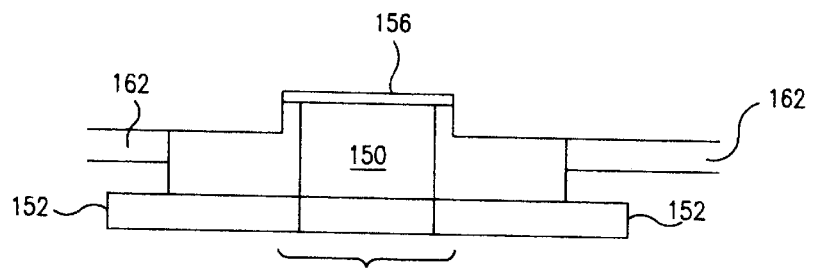
FIG. 9B
FIG. 9C
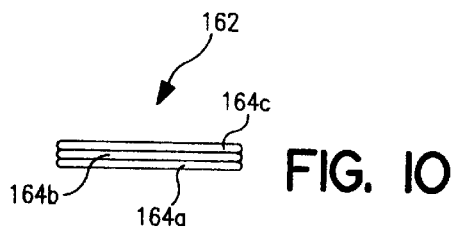
FIG. 10

FLUID SELECTION VALVE FOR A MODULAR AUTOMATED DIAGNOSTIC APPARATUS

CROSS REFERENCES TO RELATED APPLICATIONS

The present Application claims the benefit of co-pending U.S. Provisional Application No. 60/053,265, filed Jul. 21, 1997 by the same inventors as the present Application and directed to the same invention and containing the same disclosure as the present Application.

The present Patent Application is a Divisional Patent Application of, and claims benefit of, Prior patent application Ser. No. 09/118,683, filed Jun. 30, 1998, now U.S. Pat. No. 5,983,734 and assigned to Examiner R. Rauvis in Art Unit 2856 and since allowed and which is incorporated herein by reference. The present Patent Application is related to U.S. patent application Ser. No. by Vijay Mathur et al. for A FLUID ENTRY MECHANISM FOR A MODULAR AUTOMATED DIAGNOSTIC APPARATUS, U.S. patent application Ser. No. by Vijay Mathur et al. for A MODULAR SENSOR SYSTEM FOR A MODULAR AUTOMATED DIAGNOSTIC APPARATUS, and U.S. patent application Ser. No. by Vijay Mathur et al. for A REAGENT POUCH FOR USE IN A MODULAR AUTOMATED DIAGNOSTIC APPARATUS, all filed on even date with the present Patent Application.

FIELD OF THE INVENTION

The present invention is related to an automated diagnostic analyzer and, in particular, to an automated diagnostic analyzer capable of accepting biological samples from a variety of sample containers and providing automatic cleaning of the exterior and interior surfaces of the analyzer such that there is no contamination of the analyzer and with an improved internal fluidic system, an improved valve for introducing calibrants and air into the fluidic system, and a self contained reagent pack capable of storing and handling tonometered calibrants for blood gas determiation.

BACKGROUND OF THE INVENTION

An important and frequently required diagnostic analysis, such as may be performed in clinical or laboratory medical practice, is the automated chemical analysis of biological samples, and in particular biological samples containing whole cells or cellular debris, such as whole blood, plasma or seumn, or other biological fluids wherein the term fluid includes both liquids and gases. The analysis of biological samples containing cells or cellular debris saves valuable time in reaching a diagnosis and treatment by eliminating the separation step, which can be critical in an emergency situation, and reduces the cost of each analysis.

A major problem in the automated chemical analysis of samples containing whole cells or cellular debris, however, is the delivery of the samples from a sample container, such as a hypodermic tube, test tube or other sample container, and into the analysis apparatus. Biological samples, and in particular those containing cellular materials, have a tendency to leave films containing proteins and other biological molecules on the surfaces of the analysis apparatus. As a result, each of successive samples introduced into the analysis apparatus can simultaneously pick up constituents left on the surfaces from previous samples and deposit new constituents, so that a sample can be contaminated by one or more previous samples. This problem is particularly acute given the sizes of the samples customarily used in such analyzers, which are typically in the range of micro-liters.

These residual films tend to amccumlate over time, so that the problem increases as the number of samples increases, and the interaction between a given sample and the residual films from previous samples in unpredictable, depending upon the constituents of the samples and the composition of the residual films.

Methods for dealing with this problem as regards the interior surfaces of an analysis apparatus have long been available and generally involve regular washing or flushing of the interior passages and chambers of the apparatus through which the biological samples pass. A typical analysis apparatus will normally use the pumps, tubing and passages used to move the samples through the device to also move the cleaning solutions through the device, thereby insuring that all internal surfaces, passages and chambers that come in contact with the samples also come in contact with the cleaning solutions. These cleaning solutions range from mild to aggressive, usually containing strong alkaline constituents, such as bleach, or enzymatically active constituents, such as proteases. For this reason, many automated analysis devices are provided with containers, either located within the apparatus or outside the apparatus itself for storing cleaning solutions and the waste products resulting from cleaning operations.

These cleaning methods are confined to the interior surfaces of the analysis apparatus, that is, the surfaces of the passages and chambers through which the samples and reagents flow in passing from the sample entry point to the analysis sensors and the surfaces of the analysis sensors that are contacted by the samples. It will be noted, however, that the methods of the prior art for cleaning even the interior surfaces of an analysis apparatus are often inadequate to prevent interaction between a sample and the residue or residual films from previous samples and there is frequently contamination between samples and calibration reagents. In particular, the interior fluid paths of the analysis apparatus of the prior art frequently include "dead" spaces or voids that trap portions of the samples and fluids flowing therethrough and such "dead" spaces and voids are difficult to flush out or clean, so that the residues or films trapped in such areas may in turn contaminate subsequent samples. Such voids and "dead" spaces frequently occur, for example, in the corners of sharp bends in the fluid paths, in the corners formed where the fluid path changes dimensions and at sliding joints between sections of the fluid path. In addition, it is common in analysis apparatus of the prior art that the fluids pass through various moving parts in the path to the analysis sensors and such moving parts, such as sliding joints, valves and pumps, frequently contain voids and "dead" spaces that trap residues or residual films that may contaminate other fluids subsequently flowing through the apparatus.

Further, it is apparent that the samples also contact the exterior surfaces of the apparatus, in particular at or around the sample entry point where the samples first enter an analysis device, such as at the input to an aspirating probe through which the samples are drawn into the apparatus. Because these surfaces are not interior to the device, and are therefore not part of the cleaning solution path within the device, the films can build up on these surfaces in a relatively unhindered manner and will eventually cause contamination of samples.

The buildup of films and deposits on the exterior surfaces of an analysis apparatus, for example, at the sample entry point such as an aspiration probe, have been usually handled in the prior art by having the user manually wipe the contaminated surfaces. This method, however, is unsatisfactory for many reasons. For example, not only does the manual cleaning of the apparatus impose an additional task on an already too busy user, but the user may forget to clean the sample entry as often as necessary, or at all with resulting contamination of the samples. In addition, the user is undesirably exposed to biological hazards when manually cleaning the apparatus, such as puncture wounds from a contaminated aspiration probe and the sample residues themselves. The user must also safely dispose of the contaminated cleaning supplies, further adding to the cost and inconvenience of analyzing biological samples.

Another problem in the automated biological analysis apparatus of the prior art arises from the need to calibrate the analysis apparatus in order to validate the results of the sample analyses. In this regard, the cost of providing separate means for delivering the calibration samples, or calibrantes, and the samples to be analyzed into the apparatus can be unacceptable and, if the calibrante and analysis sample delivery paths are not substantially the same, the differences in the paths can introduce systematic errors in the analysis process as regards the calibrantes or the samples being analyzed, or both For these reasons, the means by which calibrantes are introduced to the analysis mechanism and sensors is generally the same as that used to introduce the samples to be analyzed and the calibrantes generally follow the same flow path as the samples. This, however, can result in cross-contamination between the calibrantes and the samples and this cross-contamination can be more critical than cross-contamination between samples. This problem is compounded where multiple calibrantes are necessary, as the means by which the calibrantes are introduced to the apparatus must include the capability of switching among the calibrantes without cross-contamination among the calibrantes or between the calibrantes and the samples to be analyzed. The problem is further compounded in that many current analyzers provide completely automatic calibration, so that the means by which the calibrantes are introduced are more complex while, at the same time, being less accessible for cleaning.

Still another problem in the automated biological analysis apparatus of the prior art arises because the biological samples to be analyzed may be provided in a variety of sample containers, such as Vacutainer tubes, syringes, capillary tubes of various sizes, and a variety of types and sizes of sample cups and beakers. While the sample entry point of the analysis apparatus should be capable of accepting samples directly from any of these containers, thereby providing users with the maximum flexibility as regards the acquisition and storage of samples, each different type of sample container places a different geometric constraint on the entry point and on the operations by which the samples are introduced into the analysis apparatus. This, in turn, has previously significantly increased the cost and complexity of the analysis apparatus and made the apparatus more complex for the user and, at times, very awkward for the user.

Yet another problem of the analysis apparatus of the prior art is in the valves used to select and route calibration and cleaning fluids, and perhaps sample fluids, into and through the analysis. In addition to the problems of the prior art discussed above, the design of such valves has generally conformed to traditional principles, using traditional materials such as metal or plastic for the body and moving parts of the valve and using traditional methods such as plastic or rubber seals, such as O-rings and washers, to prevent leakage from or into the valve passages. Such valves tend to be expensive to manufacture, require significant and frequent maintenance, and generally become unusable due to wear in a relative short time. In addition, and as discussed above, the traditional designs of such valves frequently include small voids or "dead areas", as described above, which trap films or residues of the calibration and cleaning fluids and samples flowing therethrough, so a one fluid or sample may frequently contaminate a subsequent fluid or sample.

Still another problem of the analysis devices of the prior art concerns the difficulty and complexity of the operations and actions required of a user of the apparatus, which may be regarded as "case of use" issues. One group of such issued relates directly to the analysis of individual samples and concern the convenience with which a user may use the apparatus to analyze a sample. For example, and as discussed above, the user should be able to present samples to the apparatus from a variety of types of sample containers without the need for special adaptations or operations to switch from one type of container to another. In another aspect of this same issue, it has been described that the analysis devices of the prior art generally require a user to frequently manually clean the means by which samples and calibrantes are introduced into the device, which is an inconvenient and potentially hazardous operation that would preferably be eliminated.

In yet another aspect of ease of use of an analysis apparatus or device concerns what may be referred to as the "logistic" aspects of the apparatus, that is, its portability, the ease or difficulty of suppling the apparatus with reagents and cleaning or calibration fluids, and the ease or difficulty of adapting the apparatus to perform different tests or multiple tests at the same time or to adding new analysis sensors. It is preferable that the apparatus be modular to the greatest possible extent.

To illustrate, such analysis apparatus is generally provided with replaceable reservoirs, containing calibrants, reagents and cleaning fluid and the replaceable reservoirs are sometimes combined into a unit known as a reagent or fluids pack. For the case of blood gas analyzers, however, external tans of calibrated gases are usually required in addition to the replaceable reagent pack. The elimination of external calibration gas tanks and the incorporation of the calibration gases into the claimant solutions within a modular, replaceable and self-contained reagent pack containing all reagents and calibrating solutions used in the analyses and calibrations, including the calibrants for gas sensors, is thereby advantageous. Not only would such a reagent pack be more convenient in that a reagent pack may simply be replaced as necessary, but the apparatus could be more portable.

This, however, presents certain problems in the design and construction of such reservoirs, or fluid packs, which are rarely or poorly met by the fluid packs of the prior art. Packs used to store, for example, calibration fluids used in association with the measurement of blood gases contain carefully calculated concentrations of gases. These containers must therefore prevent the escape or absorption of gases for extended periods. This requirement is even more stringent when the packs are required to be shipped under conditions, such as air freight, where the external atmospheric pressure may vary widely, as may the temperature. Another and related effect to be guarded against is the formation of gas bubbles in the containers since the escape of gases from solution will affect the calibrated concentration of gases in the fluid, even though the gases do not escape the container.

Still another problem of the prior art arises from the methods used in the prior art to prevent the escape or absorption of gases from or into a fluid by providing a gas tight metal foil liner, such as aluminum foil. While such metal liners are of value in preventing or reducing the escape or absorption of gases from or into a fluid, the metal foil itself may chemically react with the fluid, thereby destroying or undesirably altering the characteristics of the fluid stored therein.

The present invention provides a solution to these and other problems of the prior art.

SUMMARY OF THE INVENTION

The present invention is directed to a modular automated diagnostic analyzer having an analysis mechanism chassis for mounting a sensor module containing sensors, a fluid entry module for sample aspiration, a valve module for selecting fluids, a reagent pack for storage of calibrants, and a pump module for fluidic movement. The analyzer includes an improved fluidic system wherein a biological sample does not come into contact with the valve system through which calibrants and air are introduced to the fluid path, a value system utilizing an improved design and materials, a self-contained reagent pack containing calibrants, clearing solution and a waste container wherein the reagent pack, valve and fluid path are capable of storing and handling tonometered calibrants for blood gas determination, eliminating the need for external tanks of calibrant gases.

The fluid entry module includes an aspiration tube having a first section located within the analysis mechanism chassis for conducting fluids to the sensor chamber and a fluid entry module enclosing a second section of the aspiration tube rotatably mounted and rotatably connected to the first section of the aspiration tube by a fluid and gas tight seal and having a fluid entry port for the entry of fluids to the sensor chamber. The fluid entry module encloses the aspiration tube to rotate with and to slide along the aspiration tube and includes a wiping seal mounted in the fluid entry module and slidably enclosing the aspiration tube in a region extending from the fluid entry port to move along the aspiration tube, wherein the fluid entry module is rotatably and slidably engaged with the analysis mechanism chassis to move to a plurality of positions whereby a first position locates the aspiration tube entry port adjacent to a nipple for the introduction of calibration and cleaning fluids into the analysis apparatus. Others of the plurality of positions present the aspiration tube entry port for the aspiration of fluids into the analysis apparatus from a plurality of different types of sample containers and the motion of the wiping seal with respect to the aspiration tube entry port removes a residue of the aspirated fluids from the exterior surfaces of the aspiration tube when the fluid entry module is returned to the first position, the removed residue being aspirated into the analysis apparatus for disposal.

The apparatus also includes at least one sensor module mounted in the sensor chamber wherein each sensor module includes a sensor module body structured to mechanically stack and interlock vertically in the sensor chamber with other sensor module bodies. Each sensor module includes a fluid passage and a sensor element contained in the fluid passage wherein the fluid passage passes vertically through the sensor module body and is provided with a fluid tight seal at least one end of the fluid passage to form a fluid tight seal with the fluid passage of another sensor module body or with a fluid passage into or out of the sensor chamber. Each sensor module also includes electrical circuitry at least connecting the sensor element with a sensor body connector engaging with a socket mounted in the sensor chamber and providing electrical connections to electronics of the diagnostic analyzer. According to the present invention, therefore, the analysis tests performed on samples by the analysis apparatus can be selected by the selection and insertion of corresponding sensor modules into the sensor chamber.

The analysis mechanism also includes a fluid selection valve for selecting fluids from a selected one of a plurality of fluid sources for introduction to the entry port. The fluid selection valve includes a valve cylinder having a cylindrical extension extending from and coaxial with the axis of the valve cylinder to engage in a liquid and gas tight seal with the nipple for engaging with the entry port, and the valve cylinder and the cylindrical extension have a valve cylinder passage extending from the end of the cylindrical extension and along the axis of the cylinder to within the cylinder and therefrom to the rim of the cylinder. The fluid selection valve also includes a value body having a valve well enclosing the valve cylinder such that the valve cylinder can rotate in the well and a plurality of valve body passages extending from the inner wall of the valve, the valve body passages intersecting the inner wall of the valve well to align with the valve cylinder passage as the valve cylinder rotates, thereby allowing the valve cylinder passage to be selectively connected to a selected one of the valve body passages and a corresponding one of a plurality of fluid sources.

The apparatus also includes connections to the reagent pack's plurality of fluid sources. The reagent pack of the present invention includes one or more reagent pouchs, each pouch having a port body with a port opening therethrough for the extraction of fluid from the containers within the reagent pouch, the port opening including an external septum providing an external shield protecting from an accidental opening of the port opening and an internal seal to be penetrated by a tube leading to the selection valve to permit the fluid stored therein to be selectively extracted from the reagent pouch, the external septum providing a generally gas and liquid tight seal about the tube.

Each fluid container, or pouch, in the reagent pack, in turn, includes at least two walls sealed together along the edges of the sides to form a liquid container, wherein each wall includes multiple layers of materials wherein at least one layer is a thin, flexible glass material, and a port body with a port opening therethrough from the extraction of fluid from the reagent pouch. In a presently preferred embodiment, each wall is comprised of an inner layer of polyethylene, a middle layer of a glass material, and an outer layer of PET (polyethylene terephthalate) and the glass material is selected from the group of glass materials including a layer of thin, flexible glass, a material coated with silicone oxide, or KEVLAR. The port opening includes an internal septum to be penetrated by a fluid source tube leading to the fluid selection valve to permit the fluid stored therein to be selectively extracted from the reagent pouch In addition, the walls of one end of the reagent pouch are extended to form a filler neck wherein during filing of the reagent pouch with a fluid the pouch is filled up to a filler line of the filler neck and is sealed by heat and pressure applied along a sealing line below the filler line so that no bubbles are trapped in the reagent pouch.

The reagent pack of the present invention may also include a data chip positioned on the reagent pack to be read by a data chip reader mounted in the analysis apparatus wherein the data chip stores data to be read by the analysis apparatus for use in using the fluids stored in the reagent pouch.

The fluid entry module engages with the analysis mechanism chassis to control the relative motions and positions of the fluid entry module, the aspiration tube and the wiping seal. As such, the fluid entry module is placed in a first, or closed, position so that the aspiration tube is positioned in the first position and the wiping seal is located in a first position adjacent the fluid entry port. The fluid entry module can then be moved to a second position for the introduction of a fluid into the sample entry port from a test tube or similar container, whereby the aspiration tube is rotated to the second position and the wiping seal is moved along the aspiration tube and away from the fluid entry port, whereupon fluid is introduced into the entry port. The fluid entry module may then be returned to the first position, whereby the aspiration tube is rotated to the first position and the wiping seal is moved along the second section of the aspiration tube to the first position adjacent the wiping seal adjacent the entry port, so that the motion of the wiping seal removes a residue of the introduced fluid from the exterior surface of the aspiration tube when the fluid entry module is returned to the first position.

Further according to the present invention, the analyzer further includes a pump for aspirating fluids through the aspiration tube and sensor chamber and a switch for sensing the position of the fluid entry module and activating the pump when, or just before, the fluid entry module is returned to the first position. The action of the wiping seal causes the residue of the introduced fluid to accumulate on the exterior surface of the aspiration tube adjacent the fluid entry port as the fluid entry module is returned to the first position, so that the operation of the pump then draws the accumulated residue of the introduced fluid through the aspiration tube for disposal.

Still further according to the present invention the fluid entry module may be moved to a third position, so that the aspiration tube is rotated into a third position for the introduction of a fluid from a capillary tube or similar container, while the wiping seal remains in the first position adjacent the fluid entry port as the aspiration tube is rotated into the third position. According to the present invention, the interior of the wiping seal adjacent the fluid entry port is shaped to receive and form a fluid and gas tight seal with the capillary tube or similar container. In addition, the upper interior portion of the wiping seal is shaped at the juncture between the interior circumference of the wiping seal and the exterior surface of the aspiration tube such that a bead of a last aspirated fluid forms at the junction to function as a lubricant for motion of the wiping seal along the aspiration tube.

In an embodiment of the present invention, the aspiration tube is comprised of a first section located within the analysis mechanism chassis for conducting fluids to the sensor chamber and a second section enclosed within the fluid entry module and rotatably connected to the first section by a fluid and gas tight seal.

And still further, the fluid entry mechanism includes a valve having a nipple located adjacent the fluid entry port and engaging with the wiping seal in a fluid and gas tight joint when the fluid entry module is in the first position for selectively connecting selected ones of a plurality of calibration/cleaning sources to the nipple for the introduction of calibration/cleaning fluids to the aspiration tube and sensor chamber. The calibration and cleaning fluids may also include gases, such as air.

In a presently preferred embodiment, the valve cylinder and cylindrical extensions are a highly polished ceramic material and the valve body is likewise made of a highly polished ceramic material fitting with the valve cylinder to form a sliding liquid and gas tight seal, or of a resilient plastic material having an interference fit with the valve cylinder to form a sliding liquid and gas tight seal with the valve cylinder. In other embodiments, using either ceramic or plastic materials for the valve body, the seat between the valve body and the valve cylinder may be provided by a separate, resilient sealing cement, such as an O-ring.

In the presently preferred embodiment, the analyzer apparatus is configured with the valve being fluidic ally before the entry port mechanism. This positioning allows only reagents to flow through the valve, and the biological samples to be analyzed are introduced at the entry port following the valve, so that no biological fluids pass through the valve. This apparatus configuration provides a minimal number of dead volumes where biological samples can become contaminates for future reagents and samples, especially eliminating the contamination issues associated with biological samples flowing through valves where dead volumes typically exist.

Further according to the present invention, a sensor module may include an internal reservoir in association with the sensor element for storing fluids for use in operation of the sensor element and will generally include a body extension extending forward from the sensor module to be grasped by a user for insertion or removal of the sensor module from the sensor chamber.

According to the present invention, the sensor chamber includes an engagement element for selectively exerting pressure along a stack of one or more modular sensor modules in the sensor chamber to force the modular sensor modules into contact so that the fluid seals between the fluid passages of the modular sensor modules form a single gas and liquid tight passage through the sensor chamber.

Also, at least certain of the sensor modules are constructed to a standard width and a standard height while others of the sensor modules have widths or heights that are multiples of the standard width and height and at least certain of the modular sensors modules are dummy modules not having a sensor element but providing a gas and liquid tight fluid passage along the sensor chamber.

Other features, objects and advantages of the present invention will be understood by those of ordinary sill in the art after reading the following descriptions of a present implementation of the present invention, and after examining the drawings, wherein:

BRIEF DESCRIPTION OF THE DRAWINGS

FIGS. 5A through 5C are sequential diagrammatic views of the analysis mechanism chassis, the fluid entry module and the aspiration tube moving to a third position;

FIGS. 6A through 6C are sequential diagrammatic views of the analysis mechanism chassis, the fluid entry module and the aspiration tube moving to a second position;

FIG. 9A is a diagrammatic view of a reagent pack of the present invention;

FIGS. 9B to 9D are views of a port of a reagent pack of the present invention;

FIG. 10 is a cross section views of single and double walls of a reagent pack of the present invention; and, FIG. 11 is a perspective view of the modular automated diagnostic apparatus of the present invention.

DESCRIPTION OF THE INVENTION

Figure 1A:
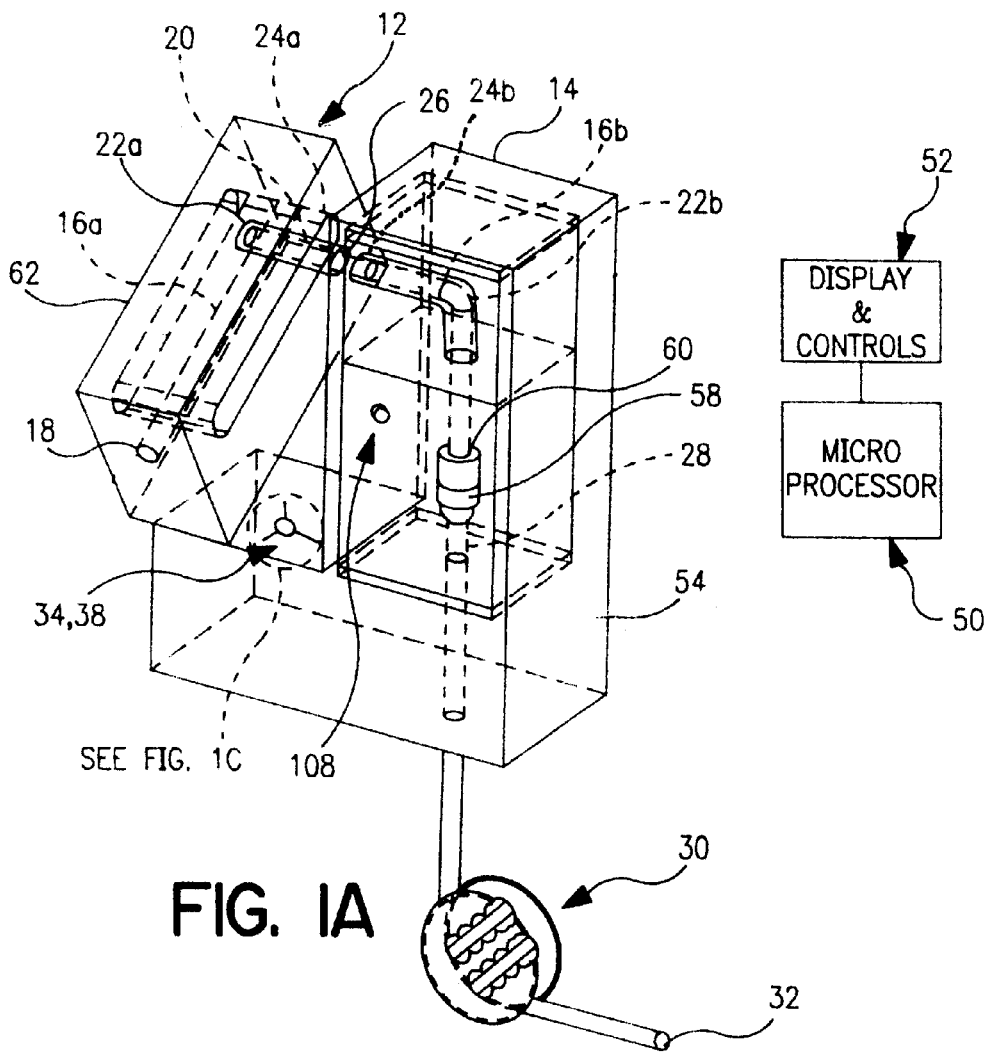
FIG. 1A is an exploded diagrammatic view of an analysis apparatus embodying the present invention and a detailed view of the aspiration tube thereof.
Figure 11:
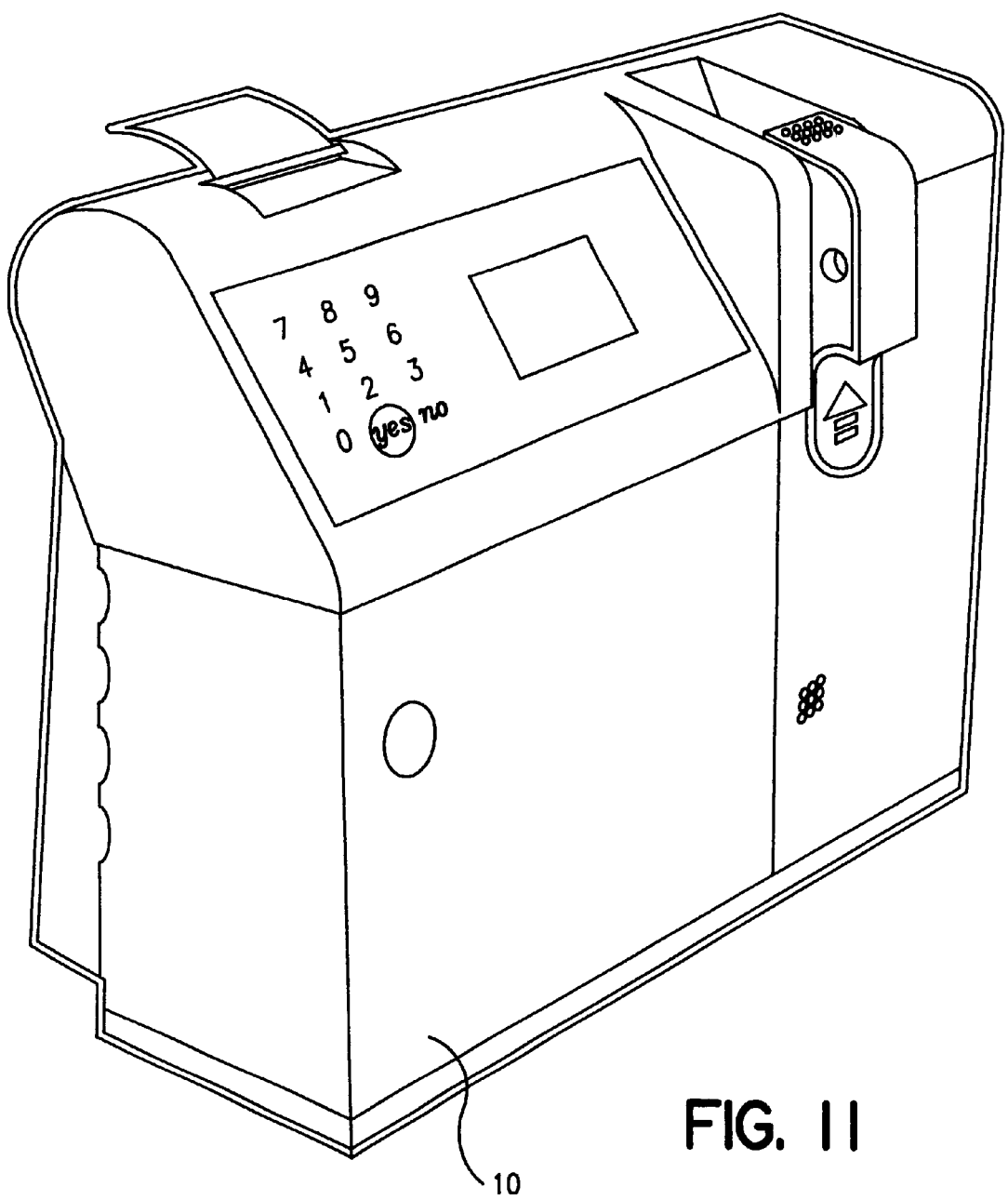

Referring to FIGS. 11 and 1A, therein is shown a diagrammatic illustration of an Analysis Apparatus 10 incorporating the present invention. Analysis Apparatus 10 is shown therein as generally comprised of a Fluid Entry Mechanism 12 and an Analysis Mechanism 14.

As illustrated in FIG. 1A, Fluid Entry Mechanism 12 includes a Aspiration Tube 16a for drawing, or aspirating, fluids including samples and calibration and cleaning solutions and gases such as air into Analysis Apparatus 10 wherein Aspiration Tube 16a is a hollow tube having an Entry Port 18 for the aspiration of the fluids. Aspiration Tube 16a extends from Entry Port 18 and to Passage Pivot 20, whereupon it enters Aspiration Tube Passage 22a leading towards Analysis Mechanism 14. As shown, Passage Pivot 20 is a generally cylindrical member having Aspiration Tube Passage 22a extending along its longitudinal center line from at least the entry point of Aspiration Tube 16a to an opening in the center of a Connecting End 24 of Passage Pivot 20.

Figure 1B:
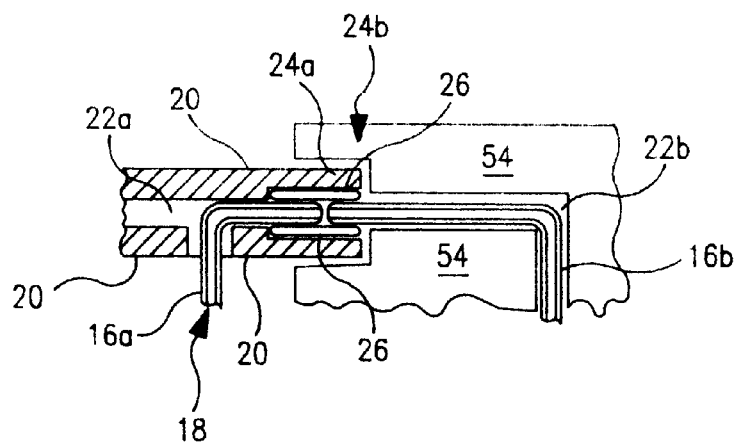
FIG. 1B is a diagrammatic view of the aspiration tube of the apparatus of the present invention.

It will be noted that, shown in FIG. 1B, Aspiration Tube 16a is curved through approximately 90° to enter Aspiration Tube Passage 22a and extend along the longitudinal axis of Aspiration Tube Passage 22a towards Connecting End 24a of Passage Pivot 20, thereby providing a continuous, smoothly contoured passage extending from Entry Port 18 to the end of Aspiration Tube 16a in the region of Connecting End 24. Aspiration Tube 16a thereby provides a passageway for the maximum, efficient transfer of fluids with the minimum entrapment of residual quantities of the fluids in the passage, as may occur, for example, at sharp corners, joints or voids along the passage.

In a present embodiment of Analysis Apparatus 10, Aspiration Tube 16a is constructed, for example, of stainless steel, polyethylene or polycarbonate and has an interior diameter of 0.032 inches and an exterior diameter of 0.042 inches to 0.063 inches. Passage Pivot 20, for example, is constructed of Delrin and has a "D" shaped cross-section with an outside radius of 0.125 inches and an overall length of 1.55 inches with Passage Pivot 20 being designed to accept and hold Aspiration Tube 16a As shown in FIG. 1A and in further detail in FIG. 1B, Aspiration Tube 16a does not, in the present embodiment of the invention, extend along Aspiration Tube Passage 22a entirely to Connecting End 24a but instead terminates within a flexible gasket or seal, indicated as Seal 26, located within an expanded section of Aspiration Tube Passage 22a at Connecting End 24a. Seal 26 and the opening therethrough that receives Aspiration Tube 16a and provides passage for fluids are, like Aspiration Tube Passage 22a, centered on the longitudinal axis of Passage Pivot 20. Seal 26 is made, for example, of butyl, viton, or silicon, and has, for example, an outside diameter of 0.094 inches and an interior diameter of 0.032 to 0.042 inches, depending upon the exterior diameter of Aspiration Tube 16a, and a length of 0.250 inches.

As illustrated in FIG. 1A, the passage for the transfer of samples, calibrantes and cleaning solutions continues into Analysis Mechanism 14 and to a Sensor Chamber 28 containing the elements for sensing the constituents of the samples. As illustrated in further detail in FIG. 1B, the passage within Analysis Mechanism 14 is provided through an Aspiration Tube 16b, which is contained within a corresponding Aspiration Tube Passage 22b, wherein the open end of Aspiration Tube 16A adjacent Connecting End 24 is aligned with Aspiration Tube 16a and the other end of Aspiration Tube 16b is smoothly bent through an angle to connect with Sensor Chamber 28. Aspiration Tube Passage 22b follows the same general path as Aspiration Tube 16b, but need not be continuously curved and may therefore be comprised of straight line segments formed in the body of Analysis Mechanism 14 by drilling or casting. As in the instance of Aspiration Tube 16a, therefore, Aspiration Tube 16b thereby provides a passageway for the maximum, efficient transfer of fluids with the minimum entrapment of residual quantities of the fluids in the passage, as may occur, for example, at sharp corners, joints or voids along the passage.

As illustrated in FIG. 1B, the end of Aspiration Tube Passage 22b nearest Connecting End 24b is enlarged to receive a section of Passage Pivot 20, such as Connecting End 24a, to a depth, for example, of 0.75 inch, so that Passage Pivot 20 rotates around the longitudinal axis defined by the longitudinal axis of Aspiration Tube Passages 22a and 22b. As also illustrated in FIG. 1B, Aspiration Tube 16b extends into this expanded section of Aspiration Tube Passage 22b, for example, for a distance of 0.25 inch, to extend into the central opening through Seal 26 to nearly mate with the corresponding end of Aspiration Tube 16a. As has been described, Seal 26 is of a resilient material and has an interior opening therethrough of approximately the same internal diameter as the internal diameters of Aspiration Tubes 16a and 16b, so that the interior diameter of the passage through Seal 26 between the ends of Aspiration Tubes 16a and 16b will be approximately the same as the interior diameters of Aspiration Tubes 16a and 16b. This construction thereby provides a gas and fluid tight rotating seal that allows Aspiration Tube 16a to rotate with respect to Aspiration Tube 16b, but without requiring precision machining or precise measurement and fitting of the components and while minimizing any voids, joints or dead spaces formed the rotating joint. This construction thereby again provides a passageway for the maximum, efficient transfer of fluids with the minimum entrapment of residual quantities of the fluids in the passage, as may occur, for example, at sharp corners, joints or voids along the fluid passageway.

As indicated in FIG. 1A, the samples, calibrantes and cleaning solutions are drawn through Aspiration Tubes 16a and 16b and through Sensor Chamber 28 by means of a Pump 30 that is connected to the opposite end of Sensor Chamber 28 from Aspiration Tube 16b and to an Exit Port 32 which ultimately leads to one or more waste receptacles for receiving the fluids, such as samples, calibrantes and cleaning solutions. In present embodiments of Analysis Apparatus 10, Sensor Chamber 28 may contain, for example, Ion Selective Electrodes, $O_2$ Electrodes, or $CO_2$ Electrodes for analyzing electrolytes or blood gases in blood samples. Pump 30 is preferably comprised of a peristaltic pump that moves fluids by moving an occlusive seal along flexible tubing, in the manner well known and understood by those of ordinary skill in the relevant arts.

It will be apparent from the above that the design of the aspiration tube passages and sensor chamber of the present invention is such that the samples, the calibration fluids and the cleaning fluids all flow through the same interior passages and that these interior passages contain no dead areas or volumes to trap the fluids flowing through the passages. In particular, it will be noted that while the passages do contain certain joints or junctures, all of the joints or junctures are of a rotating nature rather than joints or junctures allowing axial motion, thereby minimizing or eliminating the dead zones of voids arising from sharp bends in the passages or sudden changes in the diameters of the passages. The interior passages of the analysis apparatus of the present invention are thereby designed to prevent or significantly reduce the risk of contamination, or carryover, of one fluid by another.

Referring again to Fluid Entry Mechanism 12, as described above, Passage Pivot 20 and thus Aspiration Tube 16a are rotatable around the longitudinal axis of Passage Pivot 20. As indicated in FIG. 1A, Passage Pivot 20 and Aspiration Tube 16a can thereby be rotated until Entry Port 18 of Aspiration Tube 16a is aligned with, and in close proximity to, the open end of a Calibration/Cleaning Passage 34 that extends from a fluid selection valve, described in further detail below, and terminates in a stationary plastic Mipple 38 that provides a tight gas and liquid rotating seal between the rotating Calibration/Cleaning Passage 34 and the stationary Nipple 38.

Figure 1C:
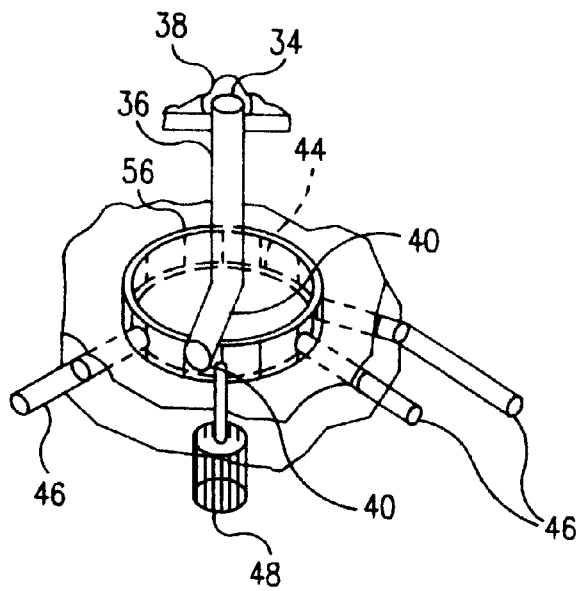
FIG. 1C is an expanded, diagrammatic and perspective view of a fluid selection valve of the present invention and the associated elements for passing selected liquids and gases into the aspiration tube of the apparatus.

As shown in greater detail in FIG. 1C, which is an enlarged perspective view of Nipple 38, Calibration/Cleaning Passage 34 and the fluid selection valve of the present apparatus, the Calibration/Cleaning Passage 34 continues therethrough to intersect with a Port 40 the outer face of cylindrical Valve Cylinder 44, so that the rotation of Valve Cylinder 44 will bring Rim Port 40 into alignment with selected ones of one or more Calibration/Cleaning Sources 46, which are fluid passages leading to one or more corresponding reservoirs for storing calibration fluids and cleaning solutions. The rotational position of Valve Cylinder 44 is controlled by a Valve Motor 48, so that Rim Port 40 and Calibration/Cleaning Passage 34 can be aligned with and thereby joined with any selected one of Cah'bration/Cleaning Sources 46, which may include a passage or opening to the air. As such, it is possible to introduce fluids or air from Calibration/Cleaning Sources 46 into Entry Port 18 and thus into the apparatus in any sequence that is desired or necessary for operation of the apparatus.

In this regard, it should be noted that Calibration/Cleaning Sources 46 will preferably include one more Calibration/Cleaning Source 46 than the number of calibration fluids and cleaning solutions to be used and that this addition Calibration/Cleaning Source 46 will be open to the ambient atmosphere so that air can be aspirated through the fluid path in the apparatus. For example, if the sensors residing in Sensor Chamber 28 are of the types having Nernstian or logarithmic characteristics with a non-zero offset, then two calibration solutions will be required, and probably one cleaning solution, so that the total number of Calibration/Cleaning Sources 46 will be 4, the fourth Calibration/Cleaning Source 46 being the connection to the atmosphere.

The provision of air as a Calibration/Cleaning Source 46 serves a number of purposes in Analysis Apparatus 10. First, a "slug" of air may be aspirated through the system between each fluid that is drawn through the apparatus, that is, between the calibration fluids, the cleaning solutions and the samples, in whatever sequence the fluids are passed through the apparatus, and the surface tension at the various fluid-air interfaces will assist in removing the fluid remnants from the internal surfaces of the apparatus. Further in this regard, the movement of air-fluid interfaces through an analysis apparatus have been proven to be effectively for general cleaning of the apparatus. Still further, separating the different fluids by air slugs prevents mixing between the fluids and thereby preserves the identities and purity of the different fluids. Finally, the use of as a "filler" between the fluids to assist in moving the fluids through the apparatus, may reduce the amounts of the fluids required, thereby conserving the fluids, allowing analysis of smaller samples, and reducing the costs of using the apparatus.

Finally, and as represented in FIG. 1A, the operation of Analysis Apparatus 10 is controlled by a Microprocessor Control Unit 50, which is connected to an associated Control and Display 52, to the sensors in Sensor Chamber 28, to Pump 30, and to Valve Motor 48, in the manner and for the operations that are well understood by those of ordinary skill in the relevant arts.

Now considering further aspects of the physical construction of Analysis Apparatus 10, it is indicated in FIG. 1A that the components of Analysis Mechanism 14 are constructed in or as part of an Analysis Mechanism Chassis 54, which forms a base and casing for Analysis Apparatus 10. The general outline and configuration of Analysis Mechanism Chassis 54, which will be described further below, is indicated in FIG. 1A in phantom lines and it will be understood by those of ordinary skill in the arts that Analysis Mechanism Chassis 54 may have a number of physical configurations, depending upon the layout and location chosen for the components of Analysis Apparatus 10, and may be constructed from a number of materials, such as aluminum, polycarbonate or acrylic. Analysis Mechanism Chassis 54 may be constructed by molding, casting or machining and drilling, or by any combination of such operations, and may be constructed of a variable number and layout of components, again depending upon the specific layout and design that is chosen In a present embodiment, for example, and as generally indicated in FIG. 1A, Analysis Mechanism Chassis 54 is constructed of aluminum and polycarbonate and is generally L shaped with an upright body, to the right, containing Connecting Tube 26, Entry Passage 20, Sensor Chamber 28, Pump 30 and Exit Port 32. The reservoir or reservoirs connected from Exit Port 32 may be located in the main body of Analysis Mechanism Chassis 54 and will generally be removable for disposal Sensor Chamber 28 may further be implemented as a replaceable component containing the sensors and the plug-in electrical connections necessary to connect the sensors to the electronic components of Analysis Apparatus 10 and having passages mating to Entry Passage 20 and connecting to Pump 30.

Further in this regard, it will be noted that both Pump 30 and the valve assembly comprising Valve Cylinder 44 and its associated structures are illustrated in FIGS. 1A and 1C in diagrammatic form and as exploded out of the Analysis Mechanism Chassis 54 for purposes of description of the structure and operation of the apparatus and that the reservoir or reservoirs connected from Exit Port 32 are not shown, for purposes of clarity. Pump 30, however, and for example, is preferably located in the lower part of the body, below Sensor Chamber 28 and one or more of Entry Passage 20, the passage to Pump 28, and the passage to Exit Port 32 may be implemented as passages drilled or cast in the body of Analysis Mechanism Chassis 54.

Figure 1D:
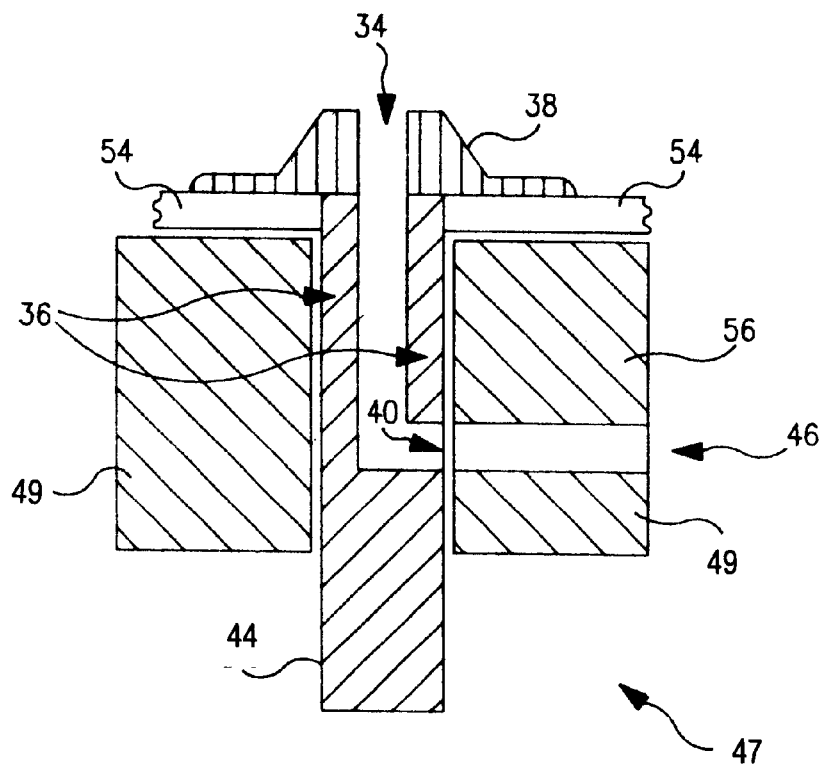
FIG. 1D is a diagrammatic cross section view of the fluid selection valve of the present invention and the associated elements of the present apparatus.

Further this regard, a presently preferred embodiment of Analysis Apparatus 10 the Calibration/Cleaning Source 46 selection valve 47 is shown in FIGS. 1A and 1C and an alternate embodiment in a cross section diagrammatic view, that is, schematically and not to dimension or proportion, in FIG. 1D. Vale 47 includes Valve Cylinder 44 and Nipple 38 and the associated elements and fluid passages associated with Valve Cylinder 44, all of which are contained in a lower extension of Analysis Mechanism Chassis 54 that extends leftwards from Analysis Mechanism 14 and under Aspiration Tube 16a and Passage Pivot 20.

As illustrated in FIG. 1C, Valve Cylinder 44 may be located in a cylindrical hole or opening forming Valve Well 56 in the body of Analysis Mechanism Chassis 54 with the passages between Port 40 of Valve Cylinder 44 and Calibration/Cleaning Sources 46 formed by passages drilled or cast into the body of Analysis Mechanism Chassis 54. The seal between Port 40 and the fluid passageways through the body of Analysis Mechanism Chassis 54 to Calibration/Cleaning Sources 46 may be formed as in any of the implementations described below.

As illustrated in FIG. 1D, Valve Cylinder 44 a includes Shaft 36, which is a cylindrical extension of Valve Cylinder 44 extending along the rotational axis of Valve Cylinder 44 from the rotational center of the upper face of Valve Cylinder 44 to Nipple 38. Valve Cylinder 44 and Shaft 36 contain Calhbration/Cleaning Passage 34 for passing selected fluids through from Port 40 in the outer wall of Valve Cylinder 44, and through Calibration/Cleaning Passage 34 to Entry Port 18 through Nipple 38.

In the presently preferred embodiment, Valve Cylinder 44 and Shaft 38 are made of a highly polished ceramic material such as alumina, and Nipple 38 is made of a resilient plastic, for example, DELRIN (Acetal). The upper end of Nipple 38, that is, the end of Nipple 38 that is adjacent to Fluid Entry Port 18, is shaped to mate with Fluid Entry Port 18 and a sealing member around Fluid Entry Port 18, as will be described further below. In the present embodiment, comprising Nipple 38 has, for example, a length of approximately 0.125 inch and a diameter of approximately 0.073 inch where it mates with Fluid Entry Port 18 and has the general shape of a truncated cone with Calabration/Cleanimg Passage 34 continuing through Nipple 38 and forming an opening in the top center of the truncated cone.

Calibration/Cleaning Passage 34 is molded or cast or drilled into Valve Cylinder 44 and Shaft 36 and has an internal diameter of approximately 0.040 inches. In the present embodiment, Valve Cylinder 44 has an outside diameter of approximately 0.500 inch and a height, or thickness, of approximately 0.200 inch and there is an extension below Valve Cylinder 44 to mate with a drive shaft driven directly or indirectly by Valve Motor 48, the drive shaft engaging extension being a disk having a diameter of approximately 0.560 inch and a height, or thickness, of approximately 0.1875 inch. In the present embodiment, the cylindrical extension comprising Shaft 36 has, for example, a length of approximately 0.5626 inch and a diameter of approximately 0.1875 inch. A section of the upper end of the cylindrical extension forming Shaft 36 has a width of approximately 0.12875 inch for a short distance just below the mating end to Nipple 38 to provide a bearing w for the rotation of the valve assembly.

It will be recognized that there are a number of ways to implement the mechanical connection between Calibration/Cleaning Sources 46 and Rim Port 40 of Calibration/Cleaning Passage 34. One implementation, shown in FIG. 1D, for example, is to construct the body of the valve as a cylindrical valve body 49 that is separate from the body of Analysis Mechanism Chassis 54 that has a cylindrical opening into which Valve Cylinder 44 fits and that has passageways leading from Port 40 to openings that are connected to Calibration/Cleaning Sources 46. This separate Valve Body 49 may even be formed as a ring around Valve Cylinder 44 with passages therethrough to mate with Port 40 and with tubing leading from the passages through the ring to Calibration/Cleaning Sources 46. Valve Body 40 may also be made of ceramic material and the internal diameter of the opening therein into which Valve Cylinder 44 fits such that the interior face of the opening in Valve Body 49 into which Valve Cylinder 44 fits and the outer face of Valve cylinder 44 are in sliding contact, so that there is a sliding seal between Port 40 and the inner face of Valve Well 56. In these implementations, wherein the valve cylinder and the valve well are of ceramic material, the tolerances on the gap between the ceramic parts must be sufficiently tight so that the sliding seal is liquid and gas tight. In the present implementation, this tolerance is in the range of 0.000075 to 0.000200 inches.

In yet another implementation of this embodiment, the Valve Body 49 may be made, for example of Teflon, and the sliding seal may be formed by making the diameter of Valve Cylinder 44 slightly larger than the interior diameter of the opening in Valve Body 49 into which Valve Cylinder 44 fits whereupon the Teflon comprising Valve Cylinder 44 will cold flow to form a gas and fluid tight sliding fit with Valve Body 49, as is well known in the art. In other possible implementations, the sliding joint between Port 40 and Valve Body 49 and the passages leading through Valve Body 49 to Calibration/Cleaning Sources 46 can be sealed by providing an O-ring or thimble gasket for a seal between Port 40 and the body of the valve.

It will be apparent from the above that the design of the valve and associated passages of the present invention is such as to contain no dead areas or volumes to trap the fluids flowing through the passages. In particular, it will be noted that while the passages do contain certain joints or junctures, all of the joints or junctures are of a rotating nature rather than joints or junctures allowing axial motion, thereby minimizing or eliminating the dead zones of voids arising from sharp bends in the passages or sudden changes in the diameters of the passages. The valve and associated passages of the analysis apparatus of the present invention are thereby designed to prevent or significantly reduce the risk of contamination of one fluid by another. It will also be noted that in the presently preferred embodiment of the valve of the present invention, the components of the valve that are subject to wear are made of ceramic material, thereby reducing the wear rate of these components and significantly increasing the use life of the valve.

Finally, it will be noted that in yet other embodiments, the valve may be rotated manually rather than by Valve Motor 48.

In summary to this point, Analysis Apparatus 10 thereby provides two paths for conducting samples and, calibration fluids and cleaning solutions through the apparatus. The first beings at Entry Port 18 whereby samples are introduced from various types of sample containers and the second is from Calibration/Cleaning Sources 46 and through the valve assembly into Entry Port 18 whereby calibrantes and cleaning solutions are introduced. These paths are thereby identical from Entry Port 18 onwards and are thus identical for all purposes regarding the passage of samples, calibrantes and cleaning solutions through the analyzer. That is, the samples to be analyzed, the calibration fluids and the cleaning solutions all come in contact with the same internal parts and passages of the apparatus, that is, the internal sections of the apparatus from Entry Port 18 and onwards through Sensor Chamber 28.

To illustrate in further detail, the calibration fluids and cleaning solutions are conveyed through the apparatus by aligning Entry Port 18 with Nipple 38 and by controlling Valve Motor 48 to rotate Valve Cylinder 44 to align Port 40 with selected Calibration/Cleaning Sources 46 in any desired sequence. When each Calibration/Cleaning Source 46 has been selected, Pump 30 will draw the selected calibration fluid or cleaning compound from the selected Calibration/Cleaning Source 46, and through the path comprised of Calibration/Cleaning Passage 34, Aspiration Tubes 16a and 16b and through Sensor Chamber 28 and Pump 30 and out Exit Port 32.

When samples to be analyzed are to be introduced into the apparatus, Entry Port 18 is rotated away from Nipple 38 by rotating Passage Pivot 20 to make Entry Port 18 accessible to the sample. Pump 30 will then draw the sample through the path comprised of Aspiration Tubes 16a and 16b, Sensor Chamber 28, and Pump 30 and out Exit Port 32.

Figure 8C:
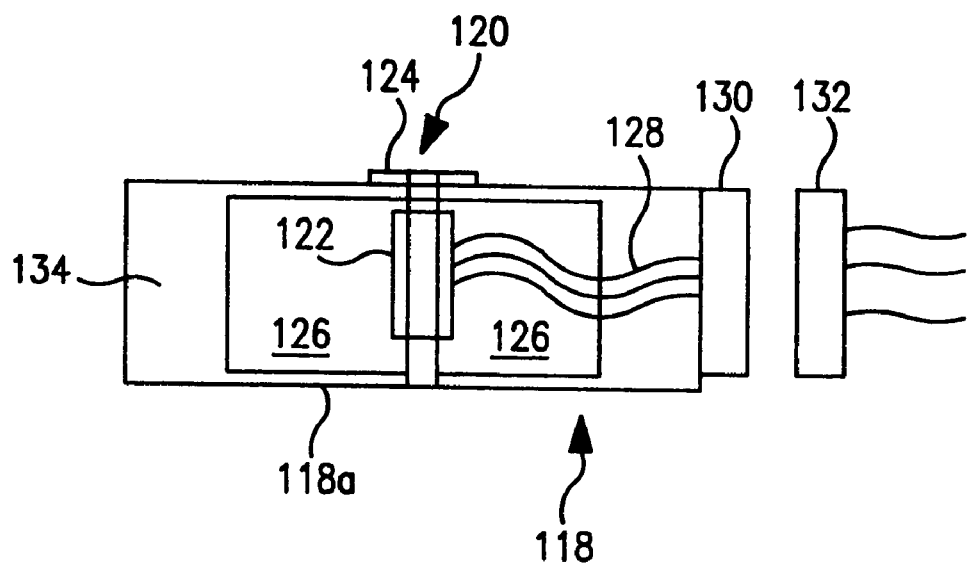
FIG. 8C is a diagrammatic cross section view of a sensor module of the present invention.
Figure 8A:
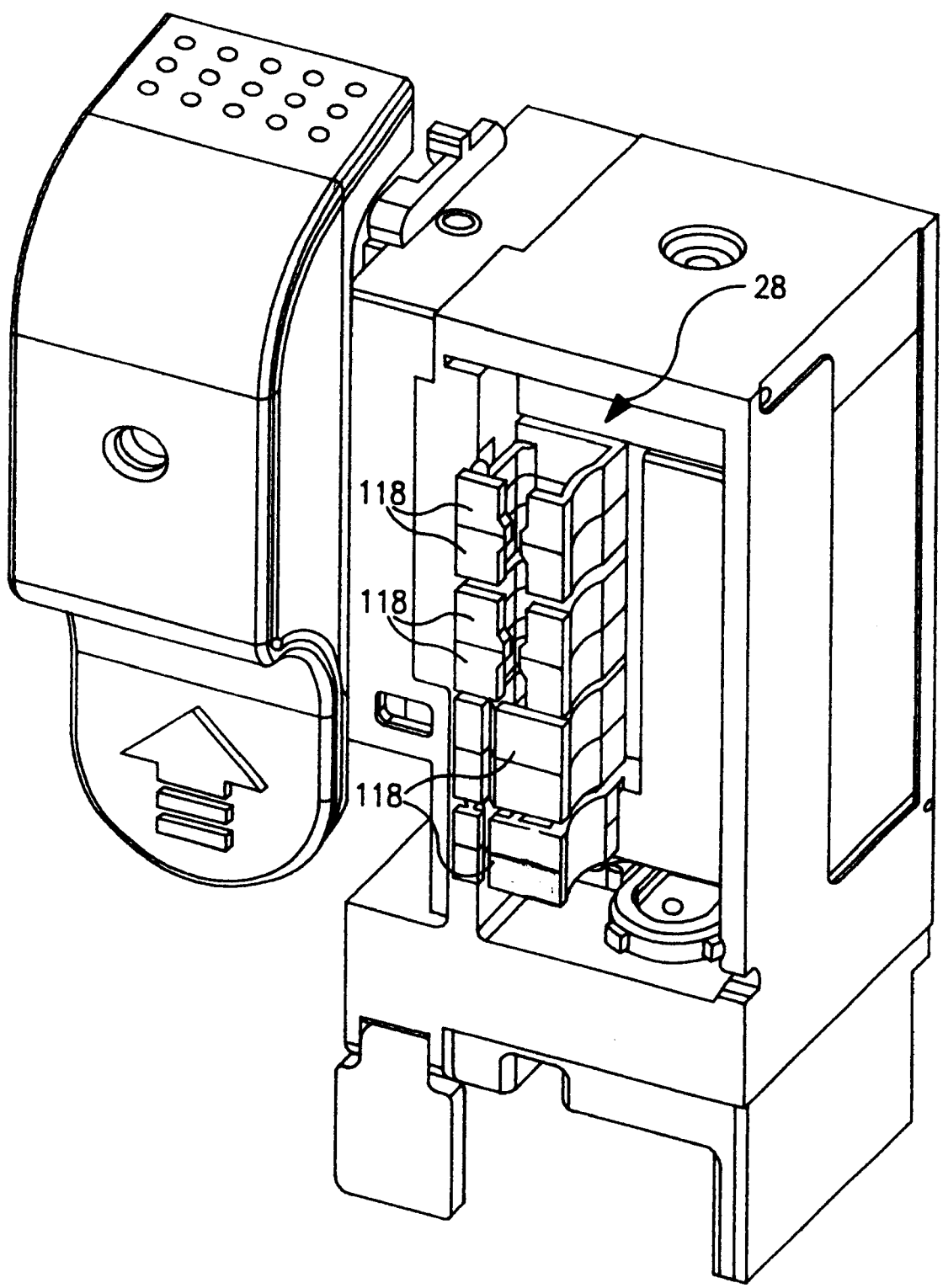
FIGS. 8A and 8B are diagrammatic perspective views of sensor and detector modules of the apparatus of the present invention.
Figure 8B:
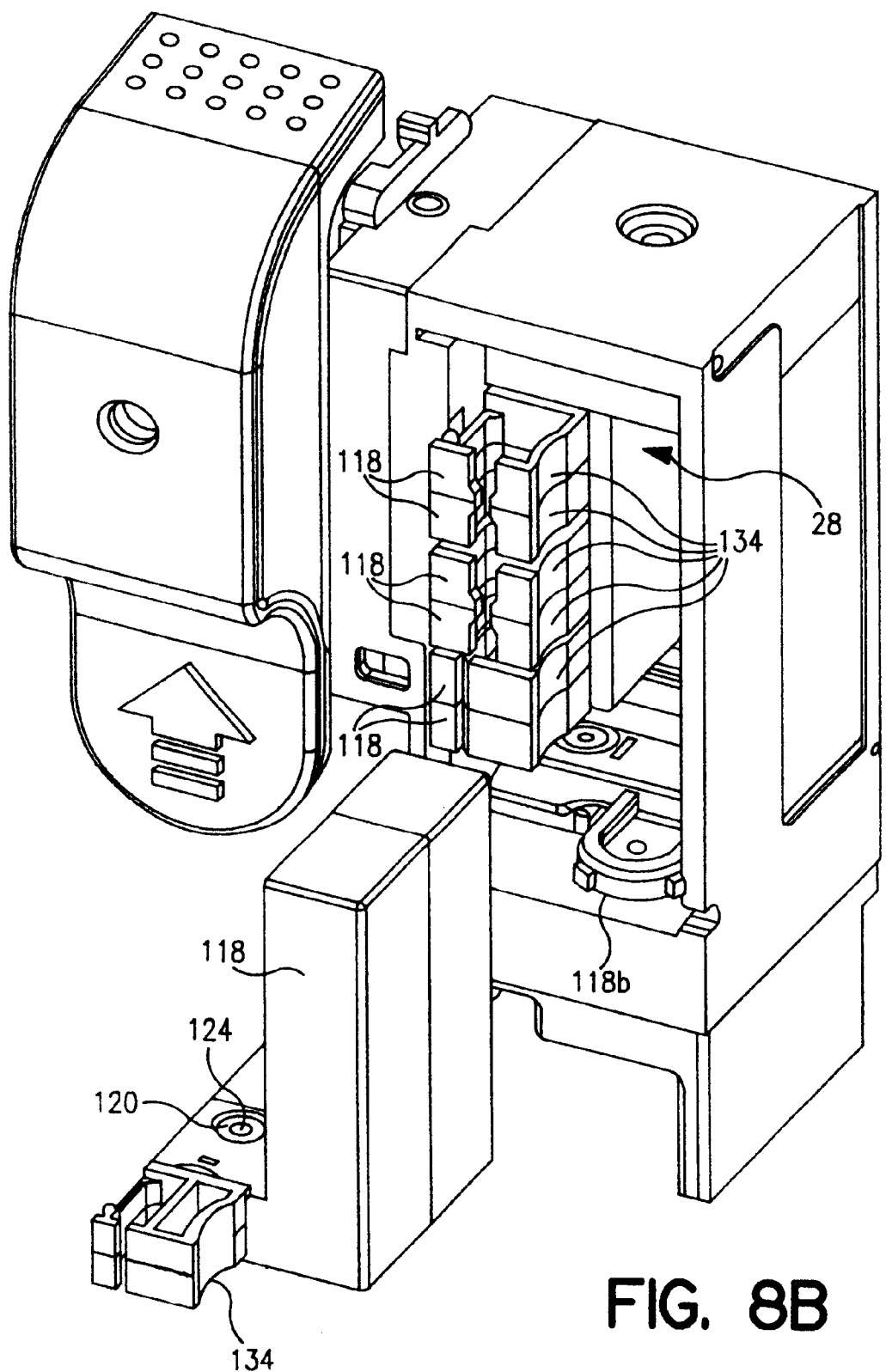

It will be noted with respect to these operations that, as indicated in FIGS. 1A, 8A and 8B. The sensors in Sensor Chamber 28 include both at least one Analysis Sensor 58 in, for example, a Sensor Module 118, and a Sample Detector 60 in, for example, a Sensor Module 118, wherein, as described above, Analysis Sensor 58 are selected, for the analysis to be performed, to detect and measure the sample constituents of interest. Sample Detector 60, in turn, is response to the presence of air-fluid interfaces in the substances flowing through Sensor Chamber 28. It should be noted that while Sample Detector 60 is illustrated in FIG. 1A as "upstream" of Analysis Sensors 58, Sample Detector 60 may also be located "downstream" of Analysis Sensors 58. A preferred embodiment would contain two Sample Detectors 60, one upstream and one downstream of the Analysis Sensors 58.

As has been described, air may be introduced into the sequence of fluids flowing through Analysis Apparatus 10, that is, between each calibration fluid, cleaning compound or sample or even at several places within sequential aliquots of the same fluid. Sample Detector 60 detects the air-fluid interfaces at the beginning and end of each sample, calibration fluid or cleaning solution and indicates these interfaces to Microprocessor Control Unit 50, which uses this information to control the flow of fluids through Sensor Chamber 28 and the sensing and measurement of the fluids thus presented to Analysis Sensors 58. Sample Detector 60, in combination with the provision of air as one of the Calibration/Cleaning Sources 46, thereby insures appropriate positioning of the various fluids with respect to Analysis Sensors 58. It will be appreciated by those of ordinary skill in the arts that various designs are available to implement Sample Detector 60, which exploits the differences in physical properties between liquids and gases. Among these are those utilizing the optical transmission and reflection properties of fluids and gases, electrical conductivity methods, and ultrasonic methods.

Having described the general and detailed design, structure and operation of Analysis Apparatus 10, the following will now describe further aspects of the structure and operation of Analysis Apparatus 10 with regard the mechanisms by which samples are introduced into Analysis Apparatus 10 from a variety of containers and by which cross contamination between samples and between samples and calibration fluids is prevented.

As has been described above, samples and calibration and cleaning solutions are introduced into Analysis Mechanism 14 by means of Aspiration Tube 16a and Passage Pivot 20, which rotate about the longitudinal axes of Passage Pivot 20 so that Entry Port 18 of Aspiration Tube 16a is presented either to Nipple 38, and thus to Calibration/Cleaning Sources 46, or to the sample containers. The only exterior section of Analysis Apparatus 10 that is thus subject to residual films and deposits is Aspiration Tube 16a around and above Entry Port 18.

Figure 3:
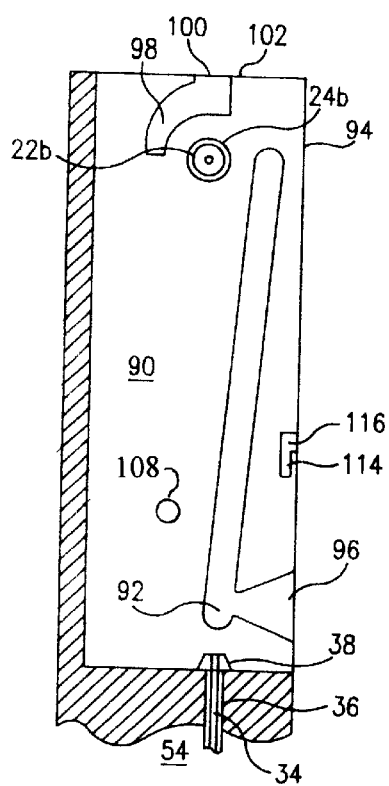
FIG. 3 is a side view of a portion of the analysis mechanism chassis of the present invention.
Figure 4:
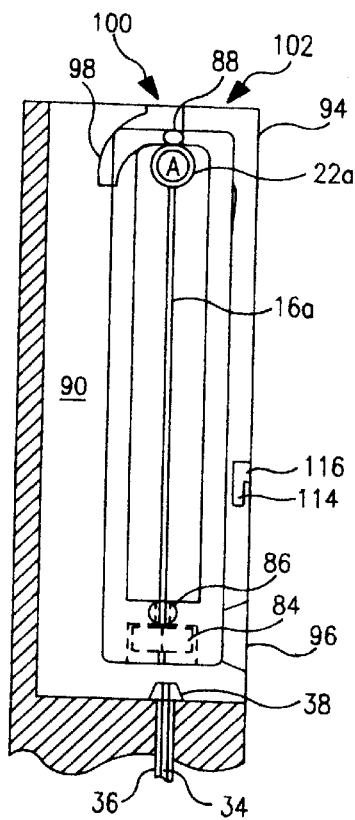
FIG. 4 is a diagrammatic view of the analysis mechanism chassis, the fluid entry module and the aspiration tube in the firm, closed position.

As indicated generally in FIG. 1A, Aspiration Tube 16a and Passage Pivot 20 are enclosed in a Fluid Entry Module 62 which is shown in FIG. 3 in cutaway view as seen from the front, using the same general viewpoint as in FIG. 1A, and in FIG. 4 in right side view, again using the same general viewpoint as in FIG. 1A. The side of Fluid Entry Module 62 that is shown in FIG. 4 is thereby the side of Fluid Entry Module 62 that is adjacent the upper part of Analysis Mechanism Chassis 54.

Figure 2A:
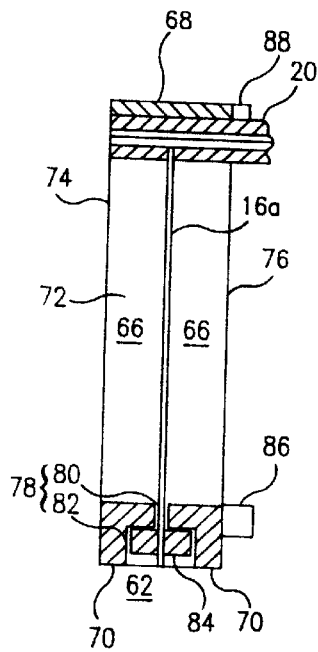
FIGS. 2A and 2B are views of the fluid entry module of the present invention.
Figure 2B:
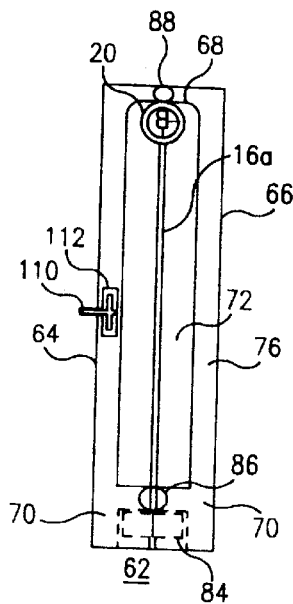

As illustrated in FIGS. 2A and 2B, Fluid Entry Module 62 is provided with a Front Wall 64, a Back Wall 66, a Top Wall 68 and a Bottom Wall 70 that together define the generally elongated rectangular body of Fluid Entry Module 62 with a Longitudinal Opening 72 extending from Side 74 to Side 76 across the width of Fluid Entry Module 62. Longitudinal Opening 72 is thus open along both Side 74 and Side 76 and is terminated at the upper end by Top Wall 68 and at the bottom end by Bottom Wall 70.

A cylindrical Aspiration Tube Opening 78 extends through Bottom Wall 70 along the longitudinal axis of Fluid Entry Module 62 and has a First Part 80 that is slightly larger than the diameter of Aspiration Tube 16a and a Second Part 82 that is sufficient diameter to accept Wiping Seal 84, which will be described in further detail below, in a press fit.

Fluid Entry Module 62 is further provided with a Lower Guide 86 protruding from the lower end of Side Wall 76 and an Upper Guide 88 protruding from the upper end of Side Wall 76, both generally located along the longitudinal axis of Fluid Entry Module 62.

As shown in FIGS. 2A and 2B, Passage Pivot 20 is located in a position within Longitudinal Opening 72 to extend across Fluid Entry Module 62 from Side Wall 76 to Side Wall 74 and, when at the extreme upper position, will abut the inner side of Top Wall 68. Aspiration Tube 16a extends from Passage Pivot 20 and along the longitudinal axis of Fluid Entry Module 62 within Longitudinal Opening 72 to extend through Aspiration Tube Opening 78 and Wiping Seal 84. The length of Aspiration Tube 16a and the distance between Top Wall 68 and Bottom Wall 70 is such that the assembly comprised of Aspiration Tube 16 and Passage Pivot 20 are enclosed within Fluid Entry Module 62, but so that Fluid Entry Module 62 can slide longitudinally up and down along Aspiration Tube 16a, while rotating together with Passage Pivot 20 and Aspiration Tube 16a, about the longitudinal axis of Passage Pivot 20.

It has been described above, and will be further described below, that Fluid Enty Module 62 and Passage Pivot 20 with Aspiration-Tube 16a are to rotate as a unit about the longitudinal axis of Passage Pivot 20. For this reason, Passage Pivot 20, as described previously, has a D shaped cross section with the flat section of the D shape engaging with the sides of Longitudinal Opening 72 provided by the walls of Side 74 and Side 76 so that Fluid Entry Module 62 rotates together with Passage Pivot 20 while being free to slide along Passage Pivot 20 in the direction of and to the extent defined by Longitudinal Opening 72.

Referring now to FIGS. 3 and 4, therein is shown a partially cutaway view of Analysis Mechanism Chassis 54 and, in particular, Body Face 90 of Analysis Mechanism Chassis 54 that is adjacent to Side Wall 76 of Fluid Entry Module 62, so that the front of Analysis Mechanism Chassis 54 and the front of Fluid Entry Module 62 face to the right of the figure. Indicated in FIG. 5 are Calibration/Cleaning Passage 34 terminating in Nipple 38, which is located in the leftwards extending lower part of Analysis Mechanism Chassis 54.

As shown in FIG. 3, Body Face 90 of Analysis Mechanism Chassis 54 is provided with a First Guide Channel 92 that is cut into Body Face 90 of Analysis Mechanism Chassis 54 to a width and depth sufficient to accept Lower Guide 86. As indicated, First Guide Channel 92 extends from just above and adjacent to Nipple 38 and continue upwards on a slant towards the Front Face 94 of Analysis Mechanism Chassis 54 to a point slightly in front of and below Entry Passage 20, ending at a point, in a present embodiment, approximately 0.094 inches distant from the center of Entry Passage 20 and downwards at approximately 45 degrees. First Guide Channel 92 also has a First Opening 96, extending from slightly above the bottom end of First Guide Channel 92 and through Front Face 94 and of sufficient width to allow the passage of Lower Guide 86.

Body Face 90 of Analysis Mechanism Chassis 54 has a Second Guide Channel 98 of sufficient depth and width to accept Upper Guide 88 and located to accept Upper Guide 88 when Fluid Entry Module 62 rotates about Passage Pivot 20 when Passage Pivot 20 is located at the upper end of Longitudinal Open 72, directly abutting Upper Wall 68. Second Guide Channel 98 extends in an approximately quarter circle path around the central axis of Passage Pivot 20 and from a point above the central axis of Passage Pivot 20 to a point that is approximately horizontally to the rear of Passage Pivot 20, relative to Front Face 94. As shown, Second Guide Channel 98 has a Second Opening 100 which extends from Second Guide Channel 98 and directly upwards from the point over Passage Pivot 20 to and through Upper Face 102 of Analysis Mechanism Chassis 54. Second Opening 100 is of sufficient width and depth to allow the passage of Upper Guide 88.

Fluid Entry Module 62 and Aspiration Tube 16a with Entry Port 18 may therefore be located in any of three positions, which may be referred to as the "closed", "capillary" and "test tube" positions, and will follow one path in moving between the "closed" position to the "capillary" position and a second path in moving between the "closed" position and the "test tube" position.

The "closed" position and the movements of Fluid Entry Module 62 and Aspiration Tube 16a with Wiping Seal 84 to the "capillary" and "test tube" positions are illustrated, respectively, in FIG. 4 and in FIGS. 5A through 5C and 6A through 6C. It will be noted that the structures and component elements shown in FIGS. 4 through 6C have been reduced to skeletal form for clarity of representation, that is, only the elements most essential to the discussion are shown and all other elements have been eliminated from these figures.

Referring to FIG. 4, and to FIGS. 2A, 2B and 3, in the "closed" position, which is the normal "at rest" position for Fluid Entry Module 62, Fluid Entry Module 62 is located in the vertical position with respect to Passage Pivot 20 and Analysis Mechanism Chassis 54 so that Entry Port 18 of Aspiration Tube 16a is directly adjacent to and mating with Nipple 38. It should be noted that, at this point, Fluid Entry Module 62 is located along Aspiration Tube 16a so that Upper Wall 68 is directly abutting Passage Pivot 20. In this "closed" position, Wiping Seal 84 is located at the lowest point along Aspiration Tube 16a, whereupon Wiping Seal 84 forms a seal with Nipple 38 to prevent leakage from this joint and the entry of unwanted substances, including air, through this joint. It will also be noted that Bottom Wall 70 preferably abuts the upper surface of Analysis Mechanism Chassis 54 around Nipple 38, with Nipple 38 extending upwards into Aspiration Tube Opening 78 to mate with Wiping Seal 84, so that the lower section of Fluid Entry Module 62 further protects this junction. In another preferred embodiment, Nipple 38 extends upwards into Aspiration Tube Opening 78, and mates with and abuts the inner surface of Wiping Seal 84 in order to minimize any dead volume therein.

Fluid Entry Module 62 and Aspiration Tube 16a with Entry Port 18 are moved to the "capillary" position, as illustrated in FIGS. 5A through 5C, by slightly lifting Fluid Entry Module 62 upwards, that is, sliding Fluid Entry Module 62 along the longitudinal axis of Aspiration Tube 16a, to the point illustrated in FIG. 5A where Fluid Entry Module 62 can rotate about Passage Pivot 20 in the manner that Lower Guide 86 passes out of First Guide Channel 92 through First Opening 96. It should be noted, in this regard, that Lower Guide 86, Upper Guide 88, First Guide Channel 92 with First Opening 96 and Second Guide Channel 94 with Second Opening 100 are preferably located and dimensioned such that Upper Guide 88 cannot yet pass through Second Opening 100 when Lower Guide 86 has reached the point to pass through First Opening 96. At this point in the motion of Fluid Entry Module 62, and as illustrated in FIG. 5B, Fluid Entry Module 62 is rotated further around Passage Pivot 20 so that Upper Guide 88 is trapped in Second Guide Channel 94 and so that Fluid Entry Module 62 cannot slide further along the longitudinal axis of Aspiration Tube 16a. In addition, and because Fluid Entry Module 62 is prevented from sliding further along Aspiration Tube 16a, the lower section of Aspiration Tube 16a, in particular Entry Port 18, will be recessed within Fluid Entry Module 62, and in particular, within Aspiration Tube Opening 78 and within Wiping Seal 84.

Fluid Entry Module 62 then continues to be rotated about Passage Pivot 20 until Entry Port 18 at the end of Aspiration Tube 16 has reached a point, illustrated in FIG. 5C, convenient for the user to present the outlet of a capillary tube, hypodermic syringe or similar sample container to Entry Port 18. In the instance of capillary tubes, for example, which are generally open at both ends, Fluid Entry Module 62 will generally be rotated until Aspiration Tube 16a is essentially horizontal so that the sample does not accidentally flow out the other end of the capillary tube and to insure the proper flow of the sample into Entry Port 18.

The end of the sample container, that is, the open end of the capillary tube, hypodermic syringe or similar container from which the sample is to be drawn, is then inserted into the opening in Wiping Seal 84 and into contact or close proximity with Entry Port 18 so that the sample can be drawn into the apparatus. It should be noted, in this respect, that the enclosure of both the open end of the sample container and Entry Port 18 within Wiping Seal 84 provides a gas and liquid sealed junction between the sample container and Entry Port 18, insuring that the sample is drawn into the apparatus and preventing the entry of air or contaminates.

Fluid Entry Module 62 and Aspiration Tube 16a with Entry Port 18 are moved to the "test tube" position, as illustrated in FIGS. 6A through 6C, by again sliding Fluid Entry Module 62 upwards along the longitudinal axis of Aspiration Tube 16a, but in this instance continuing to slide Fluid Entry Module 62 upwards past the point illustrated in FIG. 6A whereby Lower Guide 86 can pass through First Opening 96. As this motion continues, Upper Guide 88 will pass out of Second Guide Channel 94 through Second Opening 100, while Lower Guide 86 is trapped within First Guide Channel 92 and can move only upwards along First Guide Channel 92.

As Fluid Entry Module 62 continues to slide upwards along Aspiration Tube 16a, Lower Guide 86 will, as illustrated in FIG. 6B, continue to move upwards along First Guide Channel 92 and First Guide Channel 92, by constraining the motion of Lower Guide 86, will cause Fluid Entry Module 62 to slide upwards along Aspiration Tube 16a and to simultaneously rotate about Passage Pivot 20 until a significant length of Aspiration Tube 16a has been exposed and Aspiration Tube 16a has rotated to an angle, illustrated in FIG. 6C, that is convenient for the user to present a test tube, cup or similar sample container to Entry Port 18 at the end of Aspiration Tube 16, whereupon the sample is aspirated into Analysis Apparatus 10 as described above.

Finally, the above described motions of the component parts of and associated with Fluid Entry Module 62 will be reversed when Aspiration Tube 16a and Entry Port 18 are returned from the "capillary" or "test tube" positions to the "closed" position.

It is therefore apparent that the mechanism provided by Fluid Entry Module 62, Aspiration Tube 16a, Passage Pivot 20 and their related channels and guides provides an analysis apparatus that is capable of conveniently accepting samples from a wide variety of sample containers by providing an entry port mechanism with multiple positions, each position being adapted for a different class or type of sample container.

As will be described just below, this same mechanism also provides a mechanism for automatically, safely and conveniently removing the residual films and deposits from samples.

Figure 7:
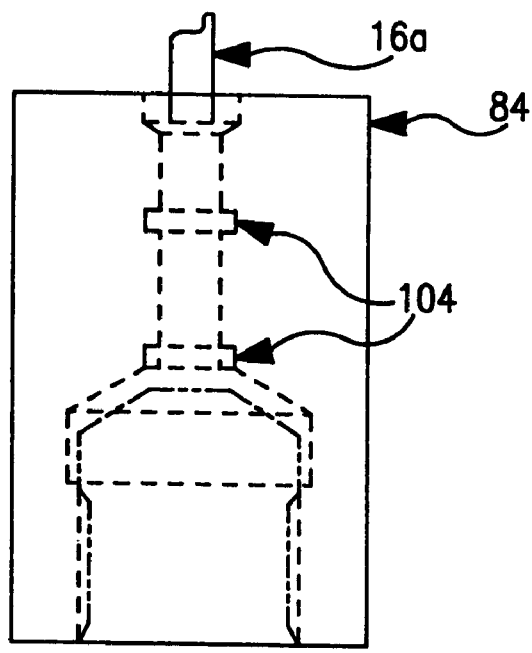
FIG. 7 is a cross-section view of the wiping seal of the present invention.

In particular, it has been described above that Wiping Seal 84 is enclosed in Aspiration Tube Opening 78, which extends through Bottom Wall 70 and that Aspiration Tube 16a extends through Wiping Seal 84 with Wiping Seal 84 sliding along Aspiration Tube 16a from and to the closed position as Entry Port 18 is moved from and to the closed position. As illustrated in FIG. 7, Wiping Seal 84 is essentially cylindrical and fits closely within Aspiration Tube Opening 78, preferably by an "interference" fit wherein the exterior diameter of Wiping Seal 84 is approximately 0.003 inches greater than the interior diameter of Aspiration Tube Opening 78, so that Wiping Seal 84 remains in place in Aspiration Tube Opening 78 as Wiping Seal 84 moves, or slides, along Aspiration Tube 16a For example, in a present embodiment of Analysis Apparatus 10 Wiping Seal 84 and Aspiration Tube Opening 78 may have respective diameters of 0.248 inch and 0.251 inch.

The interior of Wiping Seal 84 is similarly generally cylindrical, having a narrower cylindrical upper section for receiving Aspiration Tube 16a and a wider cylindrical lower section for mating with Nipple 38 and, for example, capillary tubes or syringes. As also shown in FIG. 7, the interior of the lower section of Wiping Seal 84, that is, the section of Wiping Seal 84 coming in contact with Nipple 38, is expanded and shaped internally to form a dose mating joint with Nipple 38, thereby providing a superior seal to Nipple 38 when Entry Port 18 is in the closed position, as defined above. The upper section of the interior of Wiping Seal 84, that is, the "downstream" end of Wiping Seal 84 closest to Passage Pivot 20, is fit preferably provided with one or more internally extending Sealing Ridges 104 extending around the circumference of the interior of Wiping Seal 84.

In a presently preferred embodiment, Wiping Seal 84 is preferable cast or molded from a relatively soft elastomeric material, such as silicon, Viton or butyl rubber, and the inner diameter of Sealing Ridges 104 is preferably approximately 10% to 20% smaller than the exterior diameter of Aspiration Tube 16a As such, Sealing Ridges 104 are therefore elastically expanded by Aspiration Tube 16a and thereby provide one or more corresponding seals around Aspiration Tube 16a while allowing Wiping Seal 84 to slide along Aspiration Tube 16a. It should be noted, however, that Sealing Ridges 104 are not necessary for proper operation of the apparatus and may be eliminated in alternate embodiments.

Wiping Seal 84 thereby operates when Entry Port 18 is in the dosed position to retain calibration and cleaning solutions within the interior the fluid passageways of Anaysis Apparatus 10, particularly as the calibration and cleaning solutions are present in the fluid passageways only when the calibration or cleaning solutions are aspirated through the apparatus, as discussed above. Residual films and deposits from the calibration and cleaning solutions are deposited only on the interior surfaces of the apparatus, and are thereby removed by the cleaning process. Further in this regard, it is apparent that residual films and deposits can be deposited on both the interior and exterior surfaces of the apparatus only while Entry Port 18, that is, Fluid Entry Module 62 and Aspiration Tube 16a, are in the "capillary" or "test tube" positions. It is also apparent that residual films or deposits from the samples will be deposited on the exterior surfaces of the apparatus near the tip of Aspiration Tube 16, that is, on Aspiration Tube 16a at Entry Port 18 and on the exterior surface of Aspiration Tube 16a between Entry Port 18 and the bottom of Wiping Seal 84.

It has also been described that as Entry Port 18, and thus Fluid Entry Module 62 and Aspiration Tube 16a, are moved from the "closed" position to the "capillary" or "test tube" positions, Wiping Seal 84 slides longitudinal along Aspiration Tube 16a to expose a section of Aspiration Tube 16a at and above Entry Port 18.

When a sample has been introduced into the apparatus, Entry Port 18, with Fluid Entry Module 62 and Aspiration Tube 16a, are returned to the closed position for the subsequent introduction of cleaning solutions and/or calibration fluids before the next sample is introduced As has been described above, the motion of Fluid Entry Module 62 and Aspiration Tube 16a when returning to the "closed" position are the reverse of their motions when moving to the "capillary" or "test tube" positions, so that Aspiration Tube 16 slides through Wiping Seal 84 to bring Wiping Seal 84 back to at or near the end of Aspiration Tube 16a, that is, at or near Entry Port 18. Viewed from the other perspective, Wiping Seal 84 effectively slides down Aspiration Tube 16a from the "capillary" or "test tube" position to the "closed" position and moves into close proximity with the end of Aspiration Tube 16a while doing so.

During this motion of returning to the "closed" position from the "capillary" or "test tube" positions, therefore, Wiping Seal 84 "wipes" the exterior surface of Aspiration Tube 16a, cleaning it of any residual film or deposit from the sample, with the residual film or deposit forming as a drop or bead at or very near the end of Aspiration Tube 16a, that is, at or very near Entry Port 18.

As indicated in FIGS. 1A and 3, Analysis Apparatus 10 further includes a Position Sensor 108 mounted, for example, on Face 90 of Analysis Mechanism Chassis 54, to detect when Fluid Entry Module 62 has rotated to nearly the "closed" position so that Entry Port 18, where at this point in the motion or Fluid Entry Module 62 the drop of bead of residual film or deposit from the sample has formed due to the wiping action of Wiping Seal 84, is near to but not yet in alignment and contact with Nipple 38.

At this point, Position Sensor 108 provides a signal to Microprocessor Control Unit 50, which activates Pump 30 to draw the drop or bead of sample residue or deposit into the fluid passages of Analysis Apparatus 10, whereupon it is disposed of The analysis apparatus of the present invention thereby provides an automatic system for cleaning residual sample, calibration and cleaning films and deposits from both the interior and exterior surfaces of the apparatus, thereby preventing cross contamination between samples, cabration fluids and cleaning solutions. In addition, the cleaning mechanisms of the present invention operate automatically, in particular to clean the exterior surfaces of the apparatus each time the entry port is returned to the normal closed position, and without requiring additional work on the part of the user. Still further, the cleaning mechanism of the present invention does not require that the user manually clean the apparatus, thereby avoiding risk of injury to the user and damage or contamination to the apparatus, and does not require the additional disposal of cleaning waste and materials.

Lastly, it is shown in FIGS. 3, 4 and 5 that Fluid Entry Module 62 and Analysis Mechanism Chassis 54 may additional be provided with a mechanism for selecting between operation in the "capillary" and "test tube" positions, thereby reducing the manual dexterity required on the part of the user in selecting the position of Entry Port 18 when introducing a sample into the apparatus. As illustrated therein, Front Wall 64 of Fluid Entry Module 62 is provided with a Selector Channel 110 running across Front Wall 64, generally from Side 74 to Side 76 but open on Side 76 and having a T cross section wherein the upright bar of the T intersects and opens across Front Wall 64 to form an open slot across at least part of Front Wall 64. A Selector Bar 112 having a corresponding T cross section and with the upright bar of the T extending out of the Selector Channel 110 slot extending across Front Wall is slidably mounted in Selector Channel 110 to be moved between two positions, one wherein the right hand side of Selector Bar 112 extends to the right of Side 76 to intersect Face 90 of Analysis Mechanism Chassis 54 and one wherein Selector Bar 112 is moved away from Face 90 such that it does not intersect with Face 90. Analysis Mechanism Chassis 54 is provided with a corresponding Selector Bar Channel 114 in Face 90 and preferably having an L shape as indicated in FIG. 5 with an opening 114 to Front Face 94 to receive Selector Bar 112 when Selector Bar 112 is slid towards Face 90. As a respt, when Selector Bar 112 is positioned to extend into Face 90, it will enter Selector Bar Channel 114 and prevent Entry Port Housing 62 from being rotated until Fluid Entry Module 62 has been moved upwards to the point where Lower Guide 86 cannot escape First Channel 92 through Opening 96. As a results Fluid Entry Module 62 can be moved only to the "test tube" position when Selector Bar 112 is slid to the right, but can be moved to the capillary position when Selector Bar 112 is slid to the left. It will be apparent to those of ordinary skill in the arts that the shape of Selector Bar Channel 114 and Opening 116 can be implemented in other forms to allow Fluid Entry Module 62 to slide up Aspiration Tube 16a only to the point whereby Lower Guide 86 can be rotated out through Opening 96, thereby allowing Fluid Entry Module 62 to be moved only to the "capillary" position.

Referring next to Analysis Sensors 58 and Sample Detectors 60, it has been described above that Sensor Chamber 28 preferably includes at least one Analysis Sensor 58 and at least one Sample Detector 60 and that in a presently preferred embodiment of the present apparatus Sensor Chamber 28 contains two Sample Detectors 60, one upstream and one downstream of one or more Analysis Sensors 58.

It has also been described that the Analysis Apparatus 10 of the present invention is of modular design and construction to facilitate cleaning and maintenance of the apparatus and the customization or adaptation of the apparatus to specific needs. As represented in FIGS. 8A, 8B, and 8C which are perspective views of Sensor Chamber 28 with Sensor/Detector Modules 118, this modular construction also extends to the structure and arrangement of Analysis Sensors 58 and Sample Detectors 60 which are contained in Sensor/Detector Modules 118. The modular construction and arrangement of Sensor Chamber 28 and Sensor/Detector Modules 118 thereby allows Analysis Sensors 58 and Sample Detectors 60 to be readily replaced, for example, with new Analysis Sensors 58 and Sample Detectors 60, or with different configurations of Analysis Sensors 58 and Sample Detectors 60 to meet differing needs.

As shown in FIGS. 8A, 8B and 8C, Sensor/Detector Modules 118 are each contained in a Sensor Module Body 118a designed to mechanically stack and interlock vertically in Sensor Chamber 28 to form a single assembly filling Sensor Chamber 28. As illustrated generally in FIG. 8C, which is a generic and diagrammatic cross sectional view of a Sensor/Detector Module 118, each a Sensor Module Body 118a is provided with a Fluid Passage 120 containing a Sensor Element 122, the type and specific construction and operation of each Sensor Element 122 depending upon the type of Sensor/Detector Module 118. As illustrated, each Fluid Passage 120 passes vertically completely through the Sensor Module Body 118a from the top side to the bottom side of the Sensor Module Body 118a and is provided with at least one Fluid Passage Seal 124 at least one end of Fluid Passage 120, being shown in FIG. 8C as an O-ring seal at the upper end of Fluid Passage 120.

In the present embodiment, Sensor Chamber 28 includes a sensor module Engagement Element 118b, such as a cam or spring element that exerts a force along a stack of Sensor/Detector Modules 118 so that the Fluid Passage Seal 124 at the upper end of the Fluid Passage 120 of each a Sensor Module Body 118a is forced into pressure contact with the lower surface of the Sensor Module Body 118a immediately above, or with the upper surface of Sensor Chamber 28. Fluid Passage Seals 124 thereby seal the junctions between the Fluid Passages 120 at the junctions between Sensor/Detector Modules 118 and between the topmost Sensor/Detector Module 118 and the end of Aspiration Tube 16b. Finally, it will be noted that the upper end of the passage from Sensor Chamber 28 to Pump 30, the input of which is located in the lower face or wall of Sensor Chamber 28, similarly has a Fluid Passage Seal 124 to seal the junction between the Fluid Passage 120 at the bottom of the lowest Sensor/Detector Module 118 and the passage to Pump 30. It may therefore be seen that the Fluid Passages 120 form a continuous gas and liquid tight passage from Aspiration Tube 16b to the output to Pump 30.

As also indicated in FIG. 8C, each Sensor Module Body 118a may include one or more Sensor Reservoirs 126 that may, for example, contain reagents or other fluids used in the operation of the Sensor Element 122. Each Sensor/Detector Module 118 may also include Sensor Circuitry 128 necessary for the operation of the Sensor/Detector Module 118, which may include a complete processing unit with memory and program control and which will include at least the electrical leads to connect the Sensor Element 122 to Microprocessor 50 and Display and Controls 52. For this reason, each Sensor/Detector Module 118 will typically include a Connector 130 for connecting the leads of the Sensor/Detector Module 118 to a Socket 132 mounted to the back wall of Sensor Chamber 28 and providing leads to Microprocessor 50 and Display and Controls 52 when the Sensor/Detector Module 118 is plugged into Sensor Chamber 28.

Finally, it will be noted that each Sensor/Detector Module 118 is provided with a Protrusion 134 on the front face of the Sensor/Detector Module 118 to provide a user hand grip by which a user of the apparatus may insert and remove Sensor/Detector Modules 118 into and from Sensor Chamber 28. It will be apparent that the insertion of a Sensor/Detector Module 118 into Sensor Chamber 28 or the removal of a Sensor/Detector Module from Sensor Chamber 28 will correspondingly make or break contact between the Sensor Element 122 electronics and leads and the apparatus electronics and microprocessor. It will also be apparent that the insertion or removal of a Sensor/Detector Module 118 may complete or disrupt the chain of Fluid Passages 120 between Aspiration Tube 16b and the outlet to Pump 30, and that it is necessary for each Sensor/Detector Module 118 location in Sensor/Chamber 28 to contain a Sensor/Detector Module 118, or an equivalent module providing a sealed Fluid Passage 120 in the corresponding location in order to complete the chain of Fluid Passages 120 between the end of Aspirtion Tube 16b and Pump 30.

Lastly in this regard, it will be noted that, as illustrated in FIG. 8B, one or more of Sensor/Detector Modules 118, such as the lowest Sensor/Detector Module 118 shown in FIG. 8B and designated as Sensor/Detector Module 118c, may have a height or width greater than others of Sensor/Detector Modules 118c. Such a Sensor/Detector Module 118 may have a height along the stack of Sensor/Detector Modules 118 that is a multiple of a standard Sensor/Detector Module 118 height, either because of functional requirements or to serve as a "filler" module when the available stack height for Sensor/Detector Modules 118 in Sensor Chamber 28 is not filled with Sensor/Detector Modules 118. In a like manner, it will be noted that Sensor Chamber 28 is shown as being wider than a standardized width of Sensor/Detector Modules 118, and that Sensor/Detector Module 118c is shown as extending to the right of the other Sensor/Detector Modules 118 and upwards into this additional space. This additional width of Sensor Chamber 28 allows the use of wider than standard Sensor/Detector Modules 118, for example, due to functional requirements such as an expanded reservoir for holding elertrolytes or other fluids used by the sensor.

It will also be appreciated by those of ordinary skill in the relevant arts that "blank" or "dummy" Sensor/Detector Modules 118 having only a Fluid Passage 122 therethrough with the appropriate seals may be provided and used to fill Sensor/Detector Module 118 spaces not occupied by functioning Sensor/Detector Modules 118, thereby serving to lock the functional Sensor/Detector Modules 118 into Sensor Chamber 28 and to provide a complete, sealed Fluid Passage 122 between the end of Aspiration Tube 16b and the passage to Pump 30. Lastly, it will be appreciated by those of ordinary skiff in the relevant arts that the frontal faces of Protrusions 134 may serve to mount or display text or pictorial labels and representations indicating for example, the type of Sensor/Detector Module 118 that is installed.

Lastly, it has been described that Calibration/Cleaning Sources 46 provide fluid passages leading to one or more corresponding reservoirs for storing calibration fluids and cleaning solutions and that the outlet of Pump 30 may similarly be led to a reservoir for holding the waste and residue from samples and cleaning and calibration fluids. As described, Analysis Apparatus 10 of the present invention is of modular design and construction to facilitate cleaning and maintenance of the apparatus and the customization or adaptation of the apparatus to specific needs and, for these reason, utilizes significantly improved reagent packs designed for use in this and similar types of apparatus, including the apparatus of the prior art.

Referring to FIGS. 9A and 10, therein are shown diagrammatic representation of, respectively, a Reagent Pouch 136 of the present invention and a cross section of the wall structure of a Reagent Pouch 136 of the present invention. As illustrated in FIG. 9A, a Reagent Pouch 136 has a generally bottle shaped form comprised of a rectangular Pouch Body 138 and, extending therefrom, a generally rectangular Filler Neck 140. In a typical embodiment Pouch Body 138 has a volume of approximately one liter and is approximately 13 inches high and 8 inches wide while Filler Neck 140 is approximately 5 inches high and 2 inches wide.

Reagent Pouch 136 may be constructed, for example, by cutting the two sides of a Reagent Pouch 136 out of a sheet of multi-layer material, which is described below, and by heat welding the two sides together to form the Reagent Pouch 136 with weld seams along Bottom 142 and Sides 144 or by cutting the two sides from the sheet of multi-layer material as a single piece joined along or side or bottom, folding the double outline together along one side or the base, and welding the remaining seams. For example, the two sides may be cut from the sheet of material as a joined, base-to-base outline of the two sides and folded along the base-to-base line so that, when prepared for filling, Reagent Pouch 136 would have a fold seam along Bottom 142 and heat welded seams along Sides 144. Whichever method is chosen, Filling End 146 of Filler Neck 140 left open to allow the Reagent Pouch 136 to be filled with a selected reagent, cleaning agent or other fluid.

Also, and as indicated in FIGS. 9A and 9B and 9C, each Reagent Pouch 136 is provided with a Pouch Port 145 located, for example, one side or the bottom of the Reagent Pouch 136 for extracting the enclosed reagent, electrolyte, cleaning agent or other fluid from the Reagent Pouch 136. In the exemplary embodiment illustrated in FIG. 9A, Pouch Port 145 is located on or near the Bottom 142 seam of Reagent Pouch 136, and adjacent one corner of Reagent Pouch 136. Pouch Port 145 extends through an opening or slit in Pouch Wall 162 of Reagent Pouch 136 with Pouch Wall 162 of Reagent Pouch 136 being fitted around and bonded to the outer rim or surface or Pouch Port 145, for example, by adhesive or heat sealing. FIG. 9B is a front view of a Pouch Port 145 and, as shown therein, Pouch Port 145 has a generally elliptical shape with tear-drop shaped tapered Ends 146 to provide a smooth curve and transition for the portion of Pouch Wall 162 that fits around Pouch Port 145. The shape of Pouch Port 145, and particularly of the Ends 146 of Pouch Port 145, thereby avoids forcing an abrupt change in direction of the material of Pouch Wall 162 at the point where Pouch Wall 162 meets Pouch Port 144 and a consequent gap or "wadding" or wrinkling of the material at the juncture, which can be difficult to seal and which can be a source of weakness, both as a joint and in inducing tears in the material.

Figure 9D:
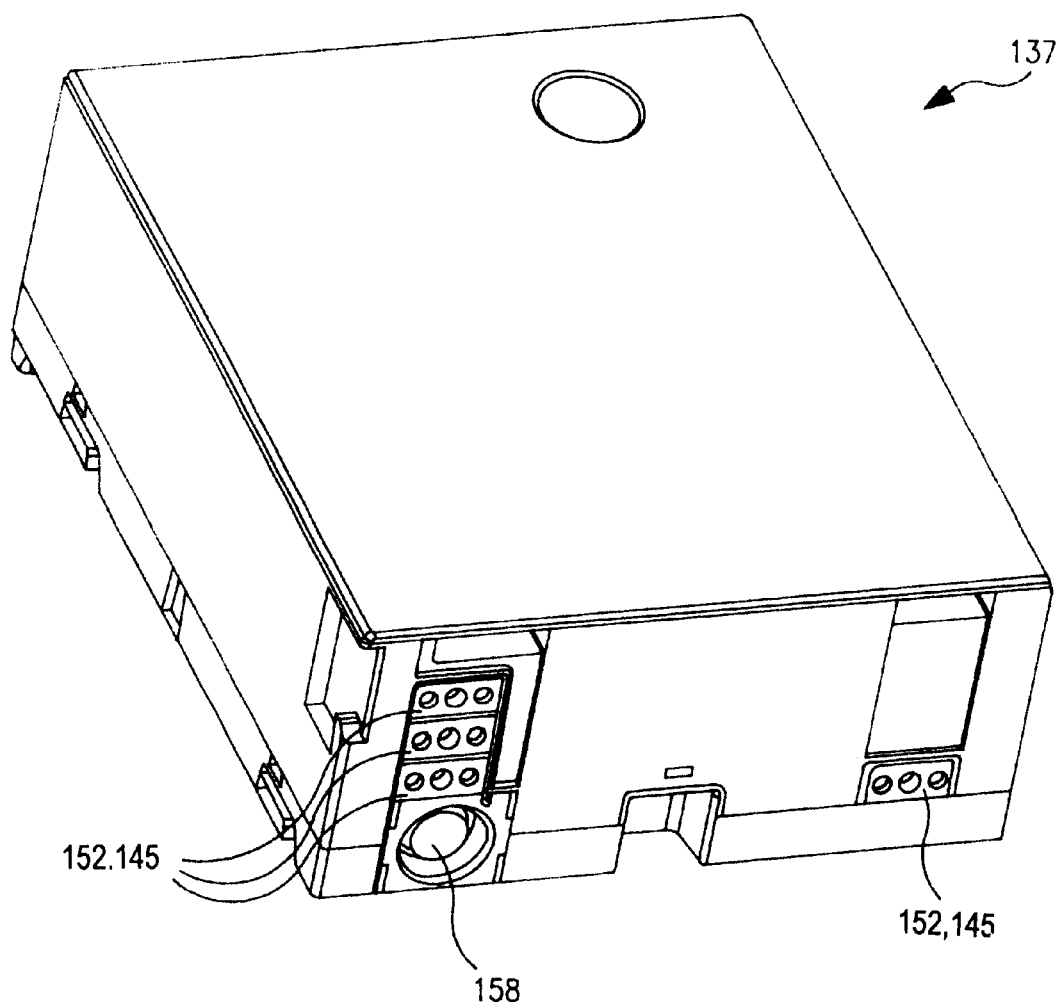

As illustrated in FIG. 9C, which is diagrammatic cross section of a Pouch Port 144, Pouch Port 145 is comprised of a Port Body 148 made, for example, of polyethylene or polypropylene, and having a Port Opening 150 therethrough for the insertion of a tube, needle or other form of passage element therethrough for extracting the fluid from Reagent Pouch 136. The outer rim of Port Body 148 is formed into an Engagement Rim 152 and, while being represented generically in FIG. 9C, is shaped to engage with a bracket within the Reagent Pouch Housing 137, an example of which is shown in FIG. 9D. As is usual and well understood in the field of art, Engagement Rim 152 operates to engage each Reagent Pouch 136 with the Reagent Pouch Housing 137 and to align Port Opening 150 with a tube, needle or other form of passage element serving to connect the corresponding Calibration/Cleaning Source 46 with the interior of the Reagent Pouch 136. Engagement Rim 152, which may be of any suitable shape, thereby operates to mechanically fix the Reagent Pouch 136 into location in the Reagent Pouch Housing 137 and to allow the tube, needle or other passage element terminating Calibration/Cleaning Sources 46 to be inserted through Port Opening 150 and into the Reagent Pouch 136. As shown, Port Opening 150 is externally covered with an External Septum 154, which may be, for example, a thin shield or membrane of the same plastic material used in Port Body 148 or any other suitable material, and which serves to protect Port Opening 150. The interior of Port Opening 150, in turn, is typically sealed with an Internal Septum 156 which may be comprised, for example, of metallic foil or, preferably, polyethelene or polyethelene covered metallic foil, and which serves to additionally seal and protect Port Opening 150. Internal Septum 156 is also designed, as well understood in the relevant arts, to form around the tube, needle or other passage element terminating Calibration/Cleaning Sources 46 as the tube or needle or element is inserted, for example, by deformation of the material around the tube or needle, to seal the joint between the tube, needle or other passage element and Internal Septum 156. Internal Septum 156 thereby operates to prevent the loss of fluid from Reagent Pouch 136 or the entry of contaminates into Reagent Pouch 136.

Lastly in this regard, it is illustrated in FIGS. 9C and 9D that one or more Reagent Pouches 136 are mounted into a Reagent Pouch Housing 137 by means of their respective Engagement Rims 152 so that the tubes, needles or other passage elements terminating the corresponding Calibration/ Sources 46 may be inserted through their respective Port Opening 150s of their Pouch Ports 144. As also illustrated in FIG. 9D, each Reagent Pouch Housing 137 is provided with a Data Chip 158 mounted on the outer surface of the Reagent Pouch Housing 137 in an area, for example, adjacent to a Pouch Port 144 or in some other suitable location. In the presently preferred embodiment, Data Chip 158 is a "smart-chip" that is used to store information regarding the contents of the Reagent Pouch Housing 137 to which it is affixed, such as an identification of the liquid or liquids stored in the Reagent Pouch Housing 137 and its particular characteristics, such as the volume and concentration of the components of the liquid or liquids, the date of manufacture, a manufacturer's identification number, and so on. Each Data Chip 158 is readable by a suitable corresponding scanner or Reader 160 mounted in the analysis apparatus in an area or location for holding a Reagent Pack 137, and in a position to be able to read the contents of the Data Chip 158 affixed to a Reagent Pack 137. There may therefore be a Data Chip 158 for and adjacent to each possible Reagent Pouch 136 location in the apparatus.

Referring now to the material comprising the walls of Reagent Pouch 136, it has been described previously that there are several major problems of the prior art regarding the use of Reagent Pouches 136. For example, in the present embodiment the fluids contained in the Reagent Pouchs 136 may include tonometered fluids, such as calibrants, composed of an electrolyte solution of known concentrations of salts, and dissolved gases of carbon dioxide, oxygen and an inert gas of known concentrations. One problem is preventing the escape of gasses from a prepared calibration fluid or test reagent, or the entry of unwanted gases, particularly during storage or transportation. Another is to avoid contact between the prepared calibration fluid or test reagent and certain of the materials commonly used to construct reagent pouches, such as the aluminum foils often used to prevent the escape of gases from the enclosed liquids, as such contact frequently results in unwanted chemical reactions. Yet another problem is that it is often difficult to obtain the necessary seals between the aluminum or other metal foils and the layers of plastic materials commonly used to construct reagent pouchs, thus resulting in another source of gas leaks from and into the pouchs.

Accordingly, and according to the present invention as illustrated in FIG. 10, the walls, or sides, of the reagent pouchs of the present invention are comprised of multiple layers of materials wherein at least one layer is a thin, flexible glass material or a silicon oxide coated material. Such glass materials have the property of being essentially gas tight for even small gas molecules, thereby providing an effective barrier to prevent the escape or introduction of gas from or into the reagent pouch, and of being chemically inert, thereby preventing or avoiding unwanted chemical reactions between the material of the reagent pouch and the fluids contained therein.

In a presently preferred embodiment of the Reagent Pouch 136 of the present invention and as illustrated in FIG. 10, a Pouch Wall 162 of a Reagent Pouch 136 is comprised of three Layers 164 wherein Inner Layer 164a is comprised, for example, of polyethelene having a thickness, for example, in the range of 50 microns, Middle Layer 164b is comprised, for example, of a glass coated material, such as 0.5 mil polyethylene coated with, a material coated with silicon oxide, such as by either evaporation or a gas plasma process, and having a coating thickness in the range of 20 microns and Outer Layer 164c is comprised, for example, of OPET having a thickness in the range of 0.5 mils. The three layers are typically bonded together in the manner well understood in the art to effectively form a single layer material made of the three layers. It will be noted that, in addition to the other advantages described above, all of these materials are or may be transparent so that the contents of the Reagent Pouch 136 are viewable.

Further, it has been described that a further problem with reagent pouches of the prior art has not only been the loss of dissolved gases from the fluids contained therein, but the formation of microbubbles of the gases within the pouches by escape of the gases from solution in the fluid therein, particularly when the reagent pouches are subjected to reduced external atmospheric pressures during shipment, such as on an airplane. As well known, this type of loss may occur despite the use of foil barrier layers to prevent the actual loss of gases from the pouches and, while the gasses are not lost from the packs, the concentration of gases within the liquid contained therein changes and the value of the liquid as a calibration standard is thereby destroyed.

Finally, it has also been described that it is necessary, or at least strongly preferable, that no gases be trapped in a Reagent Pouch 136 when it is filled with a liquid as such gases often cause unwanted changes in the composition of the gases in the liquid over time. According to the present invention, therefore, and as illustrated in FIG. 9A, a Reagent Pouch 136 is filled to a Fill Level 168 that is higher than a Filling Seat Line 170 when the Reagent Pouch 136 is first filled, and the Reagent Pouch 136 is then heat sealed along Filling Seal Line 170 by the application of heat and pressure along Filling Seal Line 170 in the manner well understood in the art. By overfilling the Reagent Pouch 136, therefore, and sealing the pack below the liquid level, therefore all extraneous gases are excluded from the Reagent Pouch 136 by the liquid filling the pouch.

Finally, FIG. 11 provides a perspective view of an assembled modular automated diagnostic apparatus of the present invention.

This concludes a description of presently preferred embodiment of the present invention, and, while the invention has been particularly shown and described with reference to selected embodiments of the apparatus thereof, it will be also understood by those of ordinary skill in the art that various changes, variations and modifications in form, details and implementation may be made therein without departing from the spirit and scope of the invention as defined by appended claims. Therefore, it is the object of the appended claims to cover all such variation and modifications of the invention as come within the true spirit and scope of the invention.

What is claimed is:

1. For use in an automated diagnostic analyzer having an analysis mechanism chassis for mounting a sensor chamber containing at least one sensor for analyzing a fluid introduced therein and an aspiration tube having an entry port for the introduction of fluids to the sensor chamber, a fluid selection valve for selecting fluids from a selected one of a plurality of fluid sources for introduction to the entry port, comprising:

a valve cylinder having a cylindrical extension extending from and coaxial with the axis of the valve cylinder to engage in a liquid and gas tight seal with a nipple for engaging with the entry port, the valve cylinder and the cylindrical extension having a valve cylinder passage extending from the end of the cylindrical extension and along the axis of the cylinder to within the cylinder and therefrom to the rim of the cylinder, and a valve body having a valve well enclosing the valve cylinder such that the valve cylinder can rotate in the well and a plurality of valve body passages extending from the inner wall of the valve well and connected to corresponding ones of the plurality of fluid sources, the valve body passages intersecting the inner wall of the valve well to align with the valve cylinder passage as the valve cylinder rotates, thereby allowing the valve cylinder passage to be selectively connected to a selected one of the valve body passages and the corresponding fluid source.

2. The fluid selection valve of claim 1 wherein the valve cylinder and cylindrical extension are formed of a polished ceramic material.

3. The fluid selection valve of claim 2 wherein the valve body is formed of a polished ceramic material having an interior diameter for forming a gas and liquid tight sliding seal with the valve cylinder.

4. The fluid selection valve of claim 2 wherein the valve body is formed of a resilient plastic material and the initial diameter of the valve cylinder is slightly larger than the interior diameter of the valve well such that the valve body will cold flow to provide a gas and fluid tight sliding seal between the valve cylinder and the inner wall of the valve well.

5. The fluid selection valve of claim 1 wherein the aspiration tube in the region of the entry port is enclosed in an entry port seal having a generally cup shaped opening to receive the nipple and the upper end of the nipple is formed to provide a gas and fluid tight seal with the mate with the entry port seal.

\* \* \* \* \*